(12) United States Patent
Briggs et al.

(10) Patent No.: US 6,576,814 B1
(45) Date of Patent: Jun. 10, 2003

(54) **MANIPULATION OF *MLO* GENES TO ENHANCE DISEASE RESISTANCE IN PLANTS**

(75) Inventors: Steven Briggs, DelMar, CA (US); Carl R. Simmons, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/347,650

(22) Filed: Jul. 6, 1999

Related U.S. Application Data

(60) Provisional application No. 60/091,875, filed on Jul. 7, 1998.

(51) Int. Cl.⁷ .................... C12N 15/09; C12N 15/29; C12N 15/82; C12N 5/04; A01H 5/00
(52) U.S. Cl. .......... 800/279; 800/278; 800/298; 800/286; 800/301; 800/320.1; 435/419; 435/468; 435/418; 536/23.1; 536/23.6; 536/24.5
(58) Field of Search ................ 800/279, 286, 800/298, 301, 320.1, 278; 435/69.1, 468, 419, 418; 536/23.1, 23.6, 24.5

(56) References Cited

U.S. PATENT DOCUMENTS 5,629,470 A * 5/1997 Lam et al. .................. 800/205
6,303,332 B1 * 10/2001 Cahoon et al. ............ 435/69.1

FOREIGN PATENT DOCUMENTS

| WO | WO 98/04586 | 2/1998 |
| WO | WO 99/23235 | 5/1999 |

OTHER PUBLICATIONS

Bennetzen et al. Genetic Engineering, vol. 14, pp. 99–124, 1992.*
Linthorst et al. The Plant Cell, vol. 1, pp. 285–291, Mar. 1989.*
Covitz et al., *Expressed Sequence Tags from a Root Hair–Enriched Medicago Trunculata cDNA Library*, Nov. 14, 1997, Database EMEST2 Online, AC/ID AA660856, Abstract XP002119426.
Walbot, V., *Maize ESTs from Various cDNA Libraries Sequenced at Stanford University*, May 17, 1999, Database EMEST2 Online, AC/ID AI668283, Abstract XP002119427.
Walbot, V., *Maize ESTs from Various cDNA Libraries Sequenced at Stanford University*, Apr. 26, 1999, Database EMEST11 Oneline, AC/ID AI621523, Abstract XP002119428.
Walbot, V. *Maize ESTs from Various Cdna Libraries sequenced at Stanford University*, May 1, 1999, Database EMEST12 Online, AC/ID ai649550, Abstract XP002119429.
Blewitt et al., *ESTs from Developing Cotton Fiber*, Jun. 12, 1999, Database EMBL Sequence Database Online, AC/ID AI729043, Abstract XP002119430.
Nemoto, Y., *Isolation of Novel Early Salt–Responding Genes from Wheat (Triticum Aestivum L.) by Differential Display*, Jul. 4, 1999, Database EMBL Sequence Database Online, AC/ID AB011444, Abstract XP002119431.
Blewitt et al, *ESTs from Developing Cotton Fiber*, Jun. 12, 1999, Database EMBL Sequence Database Online, AC/ID AI731933, Abstract XP002119432.
Buschges et al., The Barley *Mio* Gene: A Novel Control Element of Plant Pathogen Resistance, *Cell*, Mar. 7, 1997, pp. 695–705, vol. 88, Cell Press.

* cited by examiner

Primary Examiner—David T. Fox
Assistant Examiner—Medina A. Ibrahim
(74) Attorney, Agent, or Firm—Alston & Bird LLP

(57) ABSTRACT

Compositions and methods for enhancing disease resistance in plants are provided. The method involves modulating the activity of *Mlo* sequences in the plant. Particular *Mlo* sequences are provided that can be manipulated to enhance pathogen resistance in modified plants. Transformed plants, plant cells, tissues, and seed are also provided having enhanced disease resistance.

41 Claims, 5 Drawing Sheets

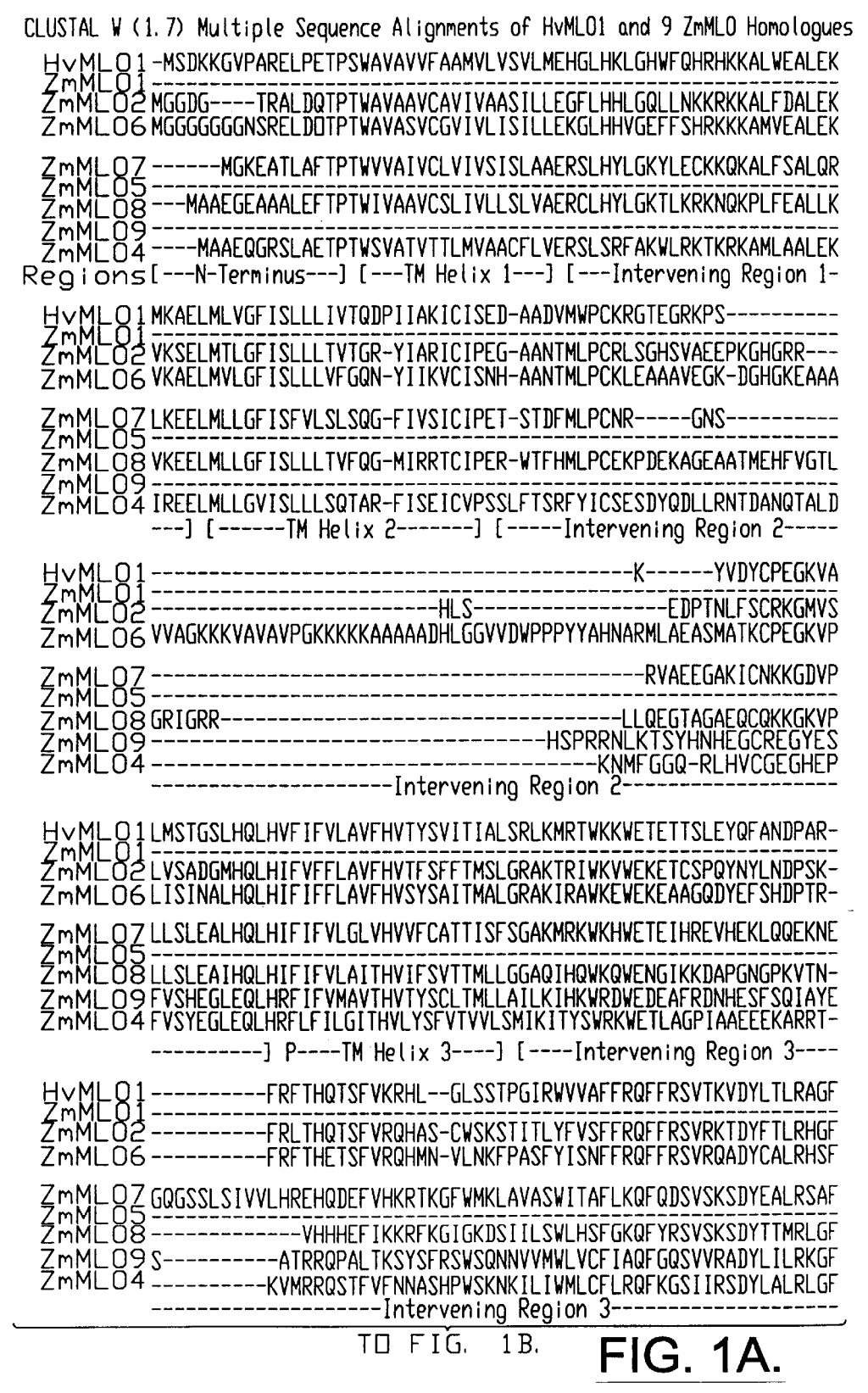

FROM FIG. 1A.

```
HvML01 INAHLSQNSKFDFHKYIKRSMEDDFKVVVGISLPLWGVAILTLFLDINGVGTLIWISFIP
ZmML01 ------------------------------------------------------------
ZmML02 ISAHLSPGTRFNFRKYIKRSLEDDFKTVVGISPPLWASALAVMLFNVHGWHNLFWFSAIP
ZmML06 VNVHLAPGSKFDFQKYIDRSLEDDFKVIVGISPPLWASALIFLFLNVNGWHTMLWISIMP

ZmML07 VVEHYPEKPDIDFHKYMTRAVEYEFKRVVGISWYLWLFVILFLLLNINGWHTYFWLAFLP
ZmML05 ------------------------------------------------------------
ZmML08 IMTHCPGNPKFDFHRYMVRVLEADFKKVVGISWYLWVFVVIFLLLNVNGWHTYFWIAFLP
ZmML09 IMTHNLPPT-YDFHNYMIRSMEEEFEKIVGVSGLLWGFVVAFMLFNVDGSNLYFWIAILP
ZmML04 MTYHKLPHS-YDFHKYMVRSMEDDYNGTIGISWPLWAYAIVCILINVHGINIYFWLSFVP
       ---Intervening Region 3---] [----TM Helix 4---] [IR 4] [-----TM HvML01 LVILLCVGTKLEMIIMEMALEIQDRAS--VIKGAPVVEPSNKFFWFHRPDWVLFFIHLTL
ZmML01 -------------------EIQDKAT--VIKGAPVVEPSDRFFWFNRPGWVLFLIHLTL
ZmML02 LVVILAVGTKLQAIIAMMAIEIAERHT--VIQGMPVVKLSDDHFWFGKPRLVLHLIHFAS
ZmML06 VVIILSVGTKLQGIICRMAIDITERHA--VIQGIPMVQVSDSYFWFARPTFVLFLIHFTL ZmML07 LFLLLIVGAKLEGIITRLAQEAAISLSN-NTEEVPKIKPCKDHFWFHKPELVLHLIHFIL
ZmML05 ------------------------------------------------------IHFIL
ZmML08 LILLLAIGTKLEHVIAQLAHDVAEKHT--AVEGDVIVKPSDEHFWFGKPRVILYLIHFIL
ZmML09 VTLVLLVGAKLQHVIATLTAEGAKMST-----YGPRIQPRDDLFWFKKPEFLLWLIHFVL
ZmML04 VELVLLVGTELQHVIAQLALEVAEATA--PY-VGSQLKLRDDLFWFGKPRVLWWLIQFIS
       Helix 5] [---------------Intervening Region 5---------------

HvML01 FQNAFQMAHFVWTVATPGLKKCYHTQIGLSIMKVVVGLALQFLCSYMTFPLYALVTQMGS
ZmML01 FQNAFQMAHFVWTLLTPDLKKCYHERLGLSIMKVAVGLVLQVLCSYITFPLYALVTQMGS
ZmML02 FQNAFEITYFFWIWYEFGLRSCFHDNFEFIIARVCLGATVQFMCSYITLPLAYALVSQMGS
ZmML06 FQNGFQIIYFLWILYEYGMDSCFNDSEEFVFARLCLGVVVQVLCSYVTLPLYALVSQMGS

ZmML07 FQNSFEISFFFWILVSEGFGSCMMERKPYVISRLVIGVIIEVECSYITLPLYAIVTHMTG
ZmML05 FQNAFEIAFFFWILTTYGFNSCIMDHVPFIVPRLVVGAIIQLLCSYSTLPLYAIVTQMGT
ZmML08 FQNAFEIAFFFWILSTYGFDSCIMGQVRFIVPRLVIGVVIQLLCSYSTLPLYAIVTQMGS
ZmML09 GQNAFELASFFWFWWQFGYDSCFIKNHLLVYCRLILGFAGQFLCSYSTLPVYALVTQMGS
ZmML04 FQNAFELATFLWSLWELSAQTCFMKHYYMVAIRLISGLLVQFWCLYYSTLPLNVIISQMGS
       -----Intervening Region 4---------] [ ------TM Helix6------] [---

HvML01 NMKRSIFDEQTSKALTNWRNTAKEKKKVR--DTDMLMAQMIGDAIPSRGSS-PMPSRGSS
ZmML01 HMKKTIFEEQTAKAVMKWRKTAKDKVRQRE-AAGFLDVLTSADTTPSHSRA-TSPSRGNS
ZmML02 EMKRTIFDEQTAKALKKWHKAVVKKKHHK-------DSSHNSSETPSTDTTGPAGEAGEW
ZmML06 TMKDSIFDEDTSKALKNWRAGAKKKAPTG-------GSKHGGGGSPTAGGS-PTKADGDA

ZmML07 QIKLHGFGSRVHESVHGWIGLRKKPFSFWKIPGGDPNADSGREADVTRRVAKERSGSSRS
ZmML05 FFKKEIFDEHVQQSLLGWAQKAKKRKALRNNGNGSNGAAAG-SSHPSATARLELMRRAVA
ZmML08 CYKKEIFNEHVQQGVLGWAQKVKMKKGLK--G-----AAS--ASKDESITNADSAGPSVK
ZmML09 KYKAALIPRRIRETIHGWGKATRKKRRRR--RGDDSTVRTETSTVCSLTDDDEDFEDDDD
ZmML04 KFKKSLVSENVRESLHSWCKRVKDRSRHN--PLFSRNGTLTTRSVCSLDTTYETDHETNT
       ----------------------C-Terminus----------------------

HvML01 ------PVHLLHKGM----------GRSDDPQSAPTSPRT------QQEARDMYPVVVAH
ZmML01 ------PVHLLHKYR----------GRSEEPQSGPASP--------GRELGDMYPVADQH
ZmML02 QRLHEVPVRHLHRYKTI-----AHVGGVRSPLSDPDYSDTDDTEPLSLQTRHLIPPAKQR
ZmML06 ------------------------------------------------------------

ZmML07 -------MPMAPADEI---------VTVDDVAVAAAAVGQGP------------------
ZmML05 -------LEEGSAGGN---------GSEASAAELHDTGPKL------------------
ZmML08 -------IEMAKAG-----------EDVEIVGNTG------------------------
ZmML09 HHHHGPSYDTPRAGGRPPYLKIETHRQSGSGHDGPRPGGTPCFHPSGSGSGHAMLLRQAS
ZmML04 VCTLSRTASATSLDDQL-----TVVTVDDEPSCIEKDV---------------------
       ---------------------C-Terminus---------------------
```

```
                          FROM FIG. 1B.
HvML01 PVHRLNPNDRRRSASSSALEADIPSADFSFSQG----------- 533 aa
ZmML01 RLHRLDP-ERMRPASSTAVNIDIADADFSFSMR------------ 224 aa
ZmML02 SLDTERAEVRVNVVETAAAPSDVLQDSFSFPRLLPPRHVPDK-- 565 aa
ZmML06 -------------------------------------------- 515 aa
ZmML07 -------------------------------------------- 499 aa
ZmML05 -------------------------------------------- 149 aa
ZmML08 -------------------------------------------- 492 aa
ZmML09 VSAPSSPSYRGGNNVTRSASMPGIAALRTTGSGTPTRVSHEEPT 469 aa
ZmML04 -------------------------------------------- 509 aa
       ---------------C-Terminus-------------------
```

FIG. 1C.

SEQUENCE LISTING

<160> NUMBER OF SEQ ID NOS: 20

<210> SEQ ID NO 1
<211> LENGTH: 845
<212> TYPE: DNA
<213> ORGANISM: Zea mays
<220> FEATURE:
<223> OTHER INFORMATION: Mlo1

<400> SEQUENCE: 1

```
aggagataca ggacaaggcg acggtcatca aggggggcgcc tgtggtggag ccaagtgaca      60
ggttcttctg gtttaaccgc cctggctggg tcctcttcct catccacctc acgctcttcc     120
agaacgcctt ccagatggcg catttcgttt ggacactgct caccccagac ctgaagaaat     180
gctaccacga gaggctgggc ctgagcatca tgaaagttgc ggtggggctg gttctccagg     240
tcctctgcag ctacatcacc ttcccgctct acgcgctcgt cacgcagatg gggtcgcaca     300
tgaagaagac catcttcgag gagcagacgg ccaaggcggt gatgaagtgg cgcaagacgg     360
ccaaggataa ggtgcggcag cgggaggcgg caggcttcct cgacgtgctg acgagcgccg     420
acaccacgcc gagccacagc cgcgcgacgt cgccgagccg gggcaactcg ccggtgcacc     480
tgctccacaa gtacagggggc aggtcggagg aaccgcagag cgggccggcg tcgccggggc     540
```

```
gggagctcgg ggacatgtac ccggtggctg accagcatcg cctgcacagg ctggaccccg      600
agaggatgag gcccgcctcg tccaccgccg tcaacattga catcgctgat gccgattttt      660
cttttagcat gcggtgacct gaccttgaac gaattctgtg tccttactct tgtataggga      720
agcaaaagca tagacggaga acataatgac acgttacgtt agggaaagtt tcgtttattc      780
atcataaaat agaatacgta ataaactagt atctccctct tcaaaaaaaa aaaaaaaaa       840 aaaaa                                                                  845

<210> SEQ ID NO 2
<211> LENGTH: 224
<212> TYPE: PRT
<213> ORGANISM: Zea mays
<220> FEATURE:
<223> OTHER INFORMATION: Mlo1

<400> SEQUENCE: 2

Glu Ile Gln Asp Lys Ala Thr Val Ile Lys Gly Ala Pro Val Val Glu
  1               5                  10                  15

Pro Ser Asp Arg Phe Phe Trp Phe Asn Arg Pro Gly Trp Val Leu Phe
             20                  25                  30

Leu Ile His Leu Thr Leu Phe Gln Asn Ala Phe Gln Met Ala His Phe
         35                  40                  45

Val Trp Thr Leu Leu Thr Pro Asp Leu Lys Lys Cys Tyr His Glu Arg
     50                  55                  60

Leu Gly Leu Ser Ile Met Lys Val Ala Val Gly Leu Val Leu Gln Val
 65                  70                  75                  80

Leu Cys Ser Tyr Ile Thr Phe Pro Leu Tyr Ala Leu Val Thr Gln Met
                 85                  90                  95

Gly Ser His Met Lys Lys Thr Ile Phe Glu Glu Gln Thr Ala Lys Ala
            100                 105                 110

Val Met Lys Trp Arg Lys Thr Ala Lys Asp Lys Val Arg Gln Arg Glu
        115                 120                 125

Ala Ala Gly Phe Leu Asp Val Leu Thr Ser Ala Asp Thr Thr Pro Ser
    130                 135                 140

His Ser Arg Ala Thr Ser Pro Ser Arg Gly Asn Ser Pro Val His Leu
145                 150                 155                 160

Leu His Lys Tyr Arg Gly Arg Ser Glu Glu Pro Gln Ser Gly Pro Ala
                165                 170                 175

Ser Pro Gly Arg Glu Leu Gly Asp Met Tyr Pro Val Ala Asp Gln His
            180                 185                 190

Arg Leu His Arg Leu Asp Pro Glu Arg Met Arg Pro Ala Ser Ser Thr
        195                 200                 205

Ala Val Asn Ile Asp Ile Ala Asp Ala Asp Phe Ser Phe Ser Met Arg
    210                 215                 220

<210> SEQ ID NO 3
<211> LENGTH: 2030
<212> TYPE: DNA
<213> ORGANISM: Zea mays
<220> FEATURE:
<223> OTHER INFORMATION: Mlo2

<400> SEQUENCE: 3
gcggcaagca attgtctcat ctgctccact ccatctccat ttaacgcact ctccactcct       60
tcgcggcggg ggtttaggcg cacggcggca ggccaattaa cgccgctgcg gcgagcaccg      120
```

-continued

| | |
|---|---|
| gggggggaaat gggcggcgac ggcacgaggg cgctggacca gacgccgacg tgggccgtgg | 180 |
| ccgccgtctg cgctgtcatc gtcgcggcgt ccatactcct cgagggcttc ctccaccacc | 240 |
| tcggtcagtt gctcaacaag aagcggaaga aggcgctgtt tgacgctctg gagaaggtta | 300 |
| aatcggagct gatgactctg gggttcatat cgctgctgct gaccgtgacg ggaaggtaca | 360 |
| tcgcgcgcat ctgcatcccg gagggagccc aaacaccat gctgccctgc cgcctgtccg | 420 |
| gtcactcggt ggcggaagag cccaagggcc atggccgacg gcacctatct gaagatccaa | 480 |
| ccaaccttt tcctgccgc aaaggcatgg tgtcgcttgt ttcagccgac ggcatgcatc | 540 |
| agctgcacat tttcgtgttc ttcttggccg tcttccatgt taccttcagt ttcttcacaa | 600 |
| tgtccttggg tagagcaaag actcgtatat ggaaggtgtg ggaaaaggaa acttgctccc | 660 |
| ctcagtataa ttatttaaat gaccccctcaa agttcaggct tacgcaccaa acatcttttg | 720 |
| tgaggcaaca tgcaagttgt tggagcaaaa gcacaatcac gctctatttt gtgagcttct | 780 |
| ttaggcagtt cttcagatcc gtccgtaaga cagactactt tactttgcga catggattca | 840 |
| tttcagctca tttatctccg gggactaggt tcaattttcg aaagtacatt aaaaggtcct | 900 |
| tggaggatga tttcaagaca gttgttggca ttagtccacc actatgggct tctgctttgg | 960 |
| ctgtcatgct gttcaatgtt catggatggc acaacttatt ctggttctct gcaattcccc | 1020 |
| ttgtagttat tctagcagtt ggaacaaagc tgcaggctat aattgctatg atggctattg | 1080 |
| aaattgcaga gaggcataca gttatccaag gcatgccggt ggtaaaacta agtgatgatc | 1140 |
| atttctggtt cgggaagcct cgtttggttc tccacctcat tcatttcgca tcatttcaga | 1200 |
| acgcatttga aattacatat ttcttttgga tctggtacga atttggcctg aggtcctgct | 1260 |
| tccatgacaa ctttgagttt atcattgcaa gagtctgcct tggggctatc gtccagttta | 1320 |
| tgtgcagcta catcacccctt ccactctatg cccttgtttc tcagatgggt tcagaaatga | 1380 |
| agcgaacaat tttcgacgag cagacagcga aggccctgaa gaaatggcac aaggccgtgg | 1440 |
| tgaagaagaa acaccacaag gattcctcac acaattcttc cgagactcct agcactgaca | 1500 |
| caacaggacc tgcaggggaa gcgggtgagt ggcagcggct gcacgaggtg ccggtccggc | 1560 |
| acctccaccg gtacaagacc atcgcgcacg tcggcggcgt gaggagcccg ttgtcggacc | 1620 |
| cggactacag cgacacggac gacaccgagc cgctgtcgtt gcagactagg cacctgatac | 1680 |
| cgccggcgaa gcagcggagc ctcgacaccg agcgcgcgga ggtgcgcgtg aacgtcgtag | 1740 |
| agacagcggc ggcgccaagc gacgtcctcc aagcacagctt ctcgttccca aggctgcttc | 1800 |
| ctcctcgcca tgtgccggac aagtaaagtg gccagcagtc tgcttagtac tacagactgt | 1860 |
| cctatataga gatagtagaa tagtagtttc aagttataag tcgatttggc tagttataca | 1920 |
| acttttgtta tttatttaga taaaggctat gtctatatag caaaagttgt aaaactagaa | 1980 |
| aaatcaaaat gatttataat ttgaaaaaaa aaaaaaaaa aaaaaaaaa | 2030 |

```
<210> SEQ ID NO 4
<211> LENGTH: 565
<212> TYPE: PRT
<213> ORGANISM: Zea mays
<220> FEATURE:
<223> OTHER INFORMATION: Mlo2

<400> SEQUENCE: 4
```

Met Gly Gly Asp Gly Thr Arg Ala Leu Asp Gln Thr Pro Thr Trp Ala
 1               5                  10                  15

Val Ala Ala Val Cys Ala Val Ile Val Ala Ala Ser Ile Leu Leu Glu
             20                  25                  30

-continued

```
Gly Phe Leu His His Leu Gly Gln Leu Leu Asn Lys Lys Arg Lys Lys
         35                  40                  45
Ala Leu Phe Asp Ala Leu Glu Lys Val Lys Ser Glu Leu Met Thr Leu
 50                  55                  60
Gly Phe Ile Ser Leu Leu Thr Val Thr Gly Arg Tyr Ile Ala Arg
 65                  70                  75                  80
Ile Cys Ile Pro Glu Gly Ala Ala Asn Thr Met Leu Pro Cys Arg Leu
                 85                  90                  95
Ser Gly His Ser Val Ala Glu Glu Pro Lys Gly His Gly Arg Arg His
                100                 105                 110
Leu Ser Glu Asp Pro Thr Asn Leu Phe Ser Cys Arg Lys Gly Met Val
                115                 120                 125
Ser Leu Val Ser Ala Asp Gly Met His Gln Leu His Ile Phe Val Phe
130                 135                 140
Phe Leu Ala Val Phe His Val Thr Phe Ser Phe Phe Thr Met Ser Leu
145                 150                 155                 160
Gly Arg Ala Lys Thr Arg Ile Trp Lys Val Trp Glu Lys Glu Thr Cys
                165                 170                 175
Ser Pro Gln Tyr Asn Tyr Leu Asn Asp Pro Ser Lys Phe Arg Leu Thr
                180                 185                 190
His Gln Thr Ser Phe Val Arg Gln His Ala Ser Cys Trp Ser Lys Ser
                195                 200                 205
Thr Ile Thr Leu Tyr Phe Val Ser Phe Arg Gln Phe Phe Arg Ser
210                 215                 220
Val Arg Lys Thr Asp Tyr Phe Thr Leu Arg His Gly Phe Ile Ser Ala
225                 230                 235                 240
His Leu Ser Pro Gly Thr Arg Phe Asn Phe Arg Lys Tyr Ile Lys Arg
                245                 250                 255
Ser Leu Glu Asp Asp Phe Lys Thr Val Val Gly Ile Ser Pro Pro Leu
                260                 265                 270
Trp Ala Ser Ala Leu Ala Val Met Leu Phe Asn Val His Gly Trp His
                275                 280                 285
Asn Leu Phe Trp Phe Ser Ala Ile Pro Leu Val Val Ile Leu Ala Val
                290                 295                 300
Gly Thr Lys Leu Gln Ala Ile Ile Ala Met Met Ala Ile Glu Ile Ala
305                 310                 315                 320
Glu Arg His Thr Val Ile Gln Gly Met Pro Val Val Lys Leu Ser Asp
                325                 330                 335
Asp His Phe Trp Phe Gly Lys Pro Arg Leu Val Leu His Leu Ile His
                340                 345                 350
Phe Ala Ser Phe Gln Asn Ala Phe Glu Ile Thr Tyr Phe Phe Trp Ile
                355                 360                 365
Trp Tyr Glu Phe Gly Leu Arg Ser Cys Phe His Asp Asn Phe Glu Phe
                370                 375                 380
Ile Ile Ala Arg Val Cys Leu Gly Ala Ile Val Gln Phe Met Cys Ser
385                 390                 395                 400
Tyr Ile Thr Leu Pro Leu Tyr Ala Leu Val Ser Gln Met Gly Ser Glu
                405                 410                 415
Met Lys Arg Thr Ile Phe Asp Glu Gln Thr Ala Lys Ala Leu Lys Lys
                420                 425                 430
Trp His Lys Ala Val Val Lys Lys His His Lys Asp Ser Ser His
                435                 440                 445
```

```
Asn Ser Ser Glu Thr Pro Ser Thr Asp Thr Thr Gly Pro Ala Gly Glu
    450                 455                 460
Ala Gly Glu Trp Gln Arg Leu His Glu Val Pro Val Arg His Leu His
465                 470                 475                 480
Arg Tyr Lys Thr Ile Ala His Val Gly Gly Val Arg Ser Pro Leu Ser
                485                 490                 495
Asp Pro Asp Tyr Ser Asp Thr Ser Asp Thr Glu Pro Leu Ser Leu Gln
            500                 505                 510
Thr Arg His Leu Ile Pro Pro Ala Lys Gln Arg Ser Leu Asp Thr Glu
        515                 520                 525
Arg Ala Glu Val Arg Val Asn Val Val Glu Thr Ala Ala Pro Ser
    530                 535                 540
Asp Val Leu Gln Asp Ser Phe Ser Phe Pro Arg Leu Leu Pro Pro Arg
545                 550                 555                 560
His Val Pro Asp Lys
                565

<210> SEQ ID NO 5
<211> LENGTH: 1841
<212> TYPE: DNA
<213> ORGANISM: Zea mays
<220> FEATURE:
<223> OTHER INFORMATION: Mlo4

<400> SEQUENCE: 5
agatatcagg gcagctggaa ctgaaggtgg cgggagccga gtgatccggc ggtgagctga      60
gcggggcggg atggcggcgg agcaggggcg gtcgctggcg gagacgccca cctggtccgt     120
ggcaaccgtc accacgctca tggtcgctgc ctgcttcctc gtcgagcgct ccctctcgcg     180
cttcgccaag tggctgcgca agaccaagcg gaaggccatg ctcgccgcgc tcgagaagat     240
ccgcgaagag ctgatgctgc tcggagtcat ctcgctgctg ctcagccaga cggcgcgctt     300
catatcggag atctgcgtgc cgtcctcgct cttcaccagc cgcttctaca tctgctccga     360
gagcgactac caggacctgc tgcgcaacac ggacgccaac cagacggcgc tcgacaagaa     420
catgttcggt ggccaacggc tgcacgtctg tggcgagggc atgaacctt tgtttcgta     480 cgagggcctt gagcagctgc accggtttct cttcatcctt ggtatcactc atgtgttgta     540
cagttttgta acagtggttc tgtccatgat caagatctat agctggagga gtgggaaac     600 cttagcaggt ccaattgctg ctgaggaatt gaaagctagg agaaccaagg tgatgagaag     660
gcagtcaacc tttgttttta acaatgcttc tcatccatgg agcaaaaata aatacttat     720 ttggatgctt tgcttttttgc gtcaattcaa gggctccata taaggtcag actatttggc     780 actgaggttg ggctttgtca catatcacaa gctaccacat tcatatgact ccataaata     840 catggtacgg agcatggaag atgattacaa tgggactatt ggtatcagtt ggccactttg     900
ggcatatgcg attgtctgca tattaatcaa tgttcatggt atcaatatat atttctggtt     960
gtcctttgtt cctgttattc tggtgcttct agtgggtact gaacttcagc acgtcattgc    1020
tcagttggct ttggaagtcg ctgaggcaac agcgccttat gttggctcac aacttaaact    1080
gcgtgatgat ctatttttggt ttggaaagcc tcgggtactc tggtggctta tacagttcat    1140
ttcatttcag aatgctttg agctggcaac attcttatgg tctctgtggg aactcagtgc    1200
acaaacatgt tcatgaagc actactacat ggttgccatt cggttgattt ctgggctcct    1260
agttcagttt tggtgcagct acagcacact gccgctgaat gtgattattt ctcagatggg    1320
ttccaagttc aagaaatcac tggtctcgga gaacgtgagg gagtcgctgc acagctggtg    1380
```

```
caagagggtt aaggacagga gccgacacaa tccgctcttc tcgcggaacg ggaccctcac    1440
gaccagatcc gtgtgctccc tagacaccac ctacgagacg gatcacgaga cgaacacggt    1500
gtgcacgctg tcgaggacgg cgtcggcgac gtcgctggac gaccagttga ccgtggtcac    1560
cgtcgatgac gagccgtcct gcattgagaa ggatgtctga cgcagttgct gattcgccaa    1620
aactacatac tgcaccgacc tgtgtgttag gaggtactct aggactgaaa tgaatgtata    1680
tgtgcagtgg ttgcccctat cgtggcagtg accatgtgta tatatagaac taaaaaaact    1740
ataatgtctc ttagctgaga gtgagaggct gtacatggaa atacttgagg cagcttggac    1800
caaatacaaa actgcatctt ttcgagaaaa aaaaaaaaa a                         1841
```

<210> SEQ ID NO 6
<211> LENGTH: 509
<212> TYPE: PRT
<213> ORGANISM: Zea mays
<220> FEATURE:
<223> OTHER INFORMATION: Mlo4

<400> SEQUENCE: 6

```
Met Ala Ala Glu Gln Gly Arg Ser Leu Ala Glu Thr Pro Thr Trp Ser
  1               5                  10                  15

Val Ala Thr Val Thr Thr Leu Met Val Ala Ala Cys Phe Leu Val Glu
             20                  25                  30

Arg Ser Leu Ser Arg Phe Ala Lys Trp Leu Arg Lys Thr Lys Arg Lys
         35                  40                  45

Ala Met Leu Ala Ala Leu Glu Lys Ile Arg Glu Glu Leu Met Leu Leu
     50                  55                  60

Gly Val Ile Ser Leu Leu Leu Ser Gln Thr Ala Arg Phe Ile Ser Glu
 65                  70                  75                  80

Ile Cys Val Pro Ser Ser Leu Phe Thr Ser Arg Phe Tyr Ile Cys Ser
                 85                  90                  95

Glu Ser Asp Tyr Gln Asp Leu Leu Arg Asn Thr Asp Ala Asn Gln Thr
            100                 105                 110

Ala Leu Asp Lys Asn Met Phe Gly Gly Gln Arg Leu His Val Cys Gly
        115                 120                 125

Glu Gly His Glu Pro Phe Val Ser Tyr Glu Gly Leu Glu Gln Leu His
    130                 135                 140

Arg Phe Leu Phe Ile Leu Gly Ile Thr His Val Leu Tyr Ser Phe Val
145                 150                 155                 160

Thr Val Val Leu Ser Met Ile Lys Ile Tyr Ser Trp Arg Lys Trp Glu
                165                 170                 175

Thr Leu Ala Gly Pro Ile Ala Ala Glu Glu Leu Lys Ala Arg Arg Thr
            180                 185                 190

Lys Val Met Arg Arg Gln Ser Thr Phe Val Phe Asn Asn Ala Ser His
        195                 200                 205

Pro Trp Ser Lys Asn Lys Ile Leu Ile Trp Met Leu Cys Phe Leu Arg
    210                 215                 220

Gln Phe Lys Gly Ser Ile Ile Arg Ser Asp Tyr Leu Ala Leu Arg Leu
225                 230                 235                 240

Gly Phe Val Thr Tyr His Lys Leu Pro His Ser Tyr Asp Phe His Lys
                245                 250                 255

Tyr Met Val Arg Ser Met Glu Asp Asp Tyr Asn Gly Thr Ile Gly Ile
            260                 265                 270

Ser Trp Pro Leu Trp Ala Tyr Ala Ile Val Cys Ile Leu Ile Asn Val
```

```
                275                 280                 285
His Gly Ile Asn Ile Tyr Phe Trp Leu Ser Phe Val Pro Val Ile Leu
            290                 295                 300
Val Leu Leu Val Gly Thr Glu Leu Gln His Val Ile Ala Gln Leu Ala
305                 310                 315                 320
Leu Glu Val Ala Glu Ala Thr Ala Pro Tyr Val Gly Ser Gln Leu Lys
                325                 330                 335
Leu Arg Asp Asp Leu Phe Trp Phe Gly Lys Pro Arg Val Leu Trp Trp
            340                 345                 350
Leu Ile Gln Phe Ile Ser Phe Gln Asn Ala Phe Glu Leu Ala Thr Phe
        355                 360                 365
Leu Trp Ser Leu Trp Glu Leu Ser Ala Gln Thr Cys Phe Met Lys His
370                 375                 380
Tyr Tyr Met Val Ala Ile Arg Leu Ile Ser Gly Leu Leu Val Gln Phe
385                 390                 395                 400
Trp Cys Leu Tyr Ser Thr Leu Pro Leu Asn Val Ile Ile Ser Gln Met
                405                 410                 415
Gly Ser Lys Phe Lys Lys Ser Leu Val Ser Glu Asn Val Arg Glu Ser
            420                 425                 430
Leu His Ser Trp Cys Lys Arg Val Lys Asp Arg Ser Arg His Asn Pro
        435                 440                 445
Leu Phe Ser Arg Asn Gly Thr Leu Thr Thr Arg Ser Val Cys Ser Leu
450                 455                 460
Asp Thr Thr Tyr Glu Thr Asp His Glu Thr Asn Thr Val Cys Thr Leu
465                 470                 475                 480
Ser Arg Thr Ala Ser Ala Thr Ser Leu Asp Asp Gln Leu Thr Val Val
                485                 490                 495
Thr Val Asp Asp Glu Pro Ser Cys Ile Glu Lys Asp Val
            500                 505
```

<210> SEQ ID NO 7
<211> LENGTH: 673
<212> TYPE: DNA
<213> ORGANISM: Zea mays
<220> FEATURE:
<223> OTHER INFORMATION: Mlo5

<400> SEQUENCE: 7

```
tgatccactt catcctcttc cagaacgcgt ttgagatcgc attcttcttc tggattctga      60
ctacctacgg tttcaactcc tgcatcatgg accacgtccc cttcattgtg ccgaggctcg     120
ttgtcgggc catcatccag ctcctctgta gctacagcac cctgcctctg tacgcgattg     180
tcacgcagat ggggactttc ttcaagaagg agatcttcga tgagcacgtg cagcagagcc     240
ttctgggctg ggcgcagaag gccaagaaga ggaaagcgct caggaacaat ggcaatggca     300
gcaatggcgc cgcggccggg tcgtcacatc catctgcgac tgcgaggctc gaactgatga     360
gacgagctgt cgctcttgaa gaaggcagtg ccggtggcaa cggagtgag gctagtgcgg      420
ccgagctaca cgacacgggc cgaagctct gaacgctgta gaaaacgccc ggcagagcgt      480
cagaagatgc agtgtttctg tacgcgagcc atatgtcact atgtcgtgtg gctgtttagc     540
caggtggtgt agtgtgatac tgcgtatcat gatttgtatg cttttctgga ttgagcttga     600
agcgtgttat ggagtgggga gctttgtgta gtgttgtgct caaaaaaaaa aaaaaaaaa     660
aaaaaaaaa aaa                                                         673
```

<210> SEQ ID NO 8
<211> LENGTH: 149
<212> TYPE: PRT
<213> ORGANISM: Zea mays
<220> FEATURE:
<223> OTHER INFORMATION: Mlo5

<400> SEQUENCE: 8

```
Ile His Phe Ile Leu Phe Gln Asn Ala Phe Glu Ile Ala Phe Phe
1               5                   10                  15

Trp Ile Leu Thr Thr Tyr Gly Phe Asn Ser Cys Ile Met Asp His Val
            20                  25                  30

Pro Phe Ile Val Pro Arg Leu Val Gly Ala Ile Ile Gln Leu Leu
            35                  40                  45

Cys Ser Tyr Ser Thr Leu Pro Leu Tyr Ala Ile Val Thr Gln Met Gly
    50                  55                  60

Thr Phe Lys Lys Glu Ile Phe Asp Glu His Val Gln Gln Ser Leu
65              70                  75                  80

Leu Gly Trp Ala Gln Lys Ala Lys Lys Arg Lys Ala Leu Arg Asn Asn
            85                  90                  95

Gly Asn Gly Ser Asn Gly Ala Ala Gly Ser Ser His Pro Ser Ala
            100                 105                 110

Thr Ala Arg Leu Glu Leu Met Arg Arg Ala Val Ala Leu Glu Glu Gly
            115                 120                 125

Ser Ala Gly Gly Asn Gly Ser Glu Ala Ser Ala Ala Glu Leu His Asp
    130                 135                 140

Thr Gly Pro Lys Leu
145
```

<210> SEQ ID NO 9
<211> LENGTH: 1815
<212> TYPE: DNA
<213> ORGANISM: Zea mays
<220> FEATURE:
<223> OTHER INFORMATION: Mlo6

<400> SEQUENCE: 9

```
aagcgatcga tagaataaat taaaggcgcg ggggcaacaa caagaatggg gggcggtggc      60
ggtggcggca actcgcggga gcttgaccag acgccgacat gggcggtggc gtcggtgtgc    120
ggcgtgatcg tgctcatctc catcctgctg gagaagggcc tccaccacgt gggcgagttc    180
ttctcccacc gcaagaagaa ggccatggtg gaggccctgg agaaggtgaa ggcggagctc    240
atggtgctgg gcttcatctc gctcctcctc gtgttcggcc agaactacat catcaaggtc    300
tgcatcagca accacgccgc caacaccatg ctcccctgca agctcgaggc cgccgccgtc    360
gagggcaagg acggccacgg caaggaggcc gccgccgtgg tcgctggcaa gaagaaggtc    420
gccgtcgccg tccctggaaa gaagaagaag aaggccgccg ccgccgccga ccatcttggc    480
ggtgtggtgg actggccgcc gccctactac gcgcacaacg ccaggatgct ggcggaggcg    540
agcatggcga ccaagtgccc cgaggggaaa gtgccgctca tctccatcaa cgccctgcac    600
cagctgcaca tcttcatctt cttcctcgcc gtcttccacg tctcctacag cgcaatcacc    660
atggcgctcg gcagggccaa gatacgtgca tggaaagagt gggagaaaga agctgcagga    720
caagactacg agttctcaca tgacccgacg cggttcaggt tcacccacga gcttccttc    780
gtgaggcagc atatgaatgt gctgaacaag tcccagcat cattctacat cagcaacttc    840
ttccggcagt tcttcaggtc cgtgaggcag gcagactact gcgcgctgcg ccacagcttt    900
```

-continued

```
gtcaacgtcc atctggcccc tgcagcaag tttgatttcc agaagtacat caagcggtct      960
ctggaggatg acttcaaggt gatcgtgggg atcagtcctc ctctgtgggc ttctgctctc     1020
atcttcctct tcctcaacgt caatggatgg cacaccatgc tctggatctc catcatgccg     1080
gtggtgatca tcctgtcggt ggggacgaag ctgcaggca tcatctgccg catggcgatc      1140
gacatcacgg agcgccacgc cgtcatccag ggcatcccga tggtgcaagt cagcgactcc     1200
tacttctggt tcgcacgccc caccttcgtg ctcttcctca tccacttcac cctcttccag     1260
aatggcttcc agatcatcta cttcctctgg attctgtatg agtacggcat ggactcgtgc     1320
ttcaacgact ccgaagagtt cgtctttgca cgactctgcc ttggcgtggt tgtccaggtg     1380
ctgtgcagct acgtgacgct cccgctgtac gcgctcgtct cccaaatggg ctccaccatg     1440
aagcagtcca tcttcgacga gcagacctcc aaggcgctca gaactggcg cgccggcgcc      1500 aagaagaagg ctcccaccgg cggctccaag cacggcggtg gtggctcccc caccgccggc     1560
ggcagcccca ccaaggccga cggcgacgcg tagagaggaa cacgctaact ttaatttctg     1620
tgtgcttaat tgcctaggct cgttaagtca gaacatgcat gcatgtaaca ccactgctgg     1680
ttttcatata gtgtcgacag atggtcaacg tacttttgc gatcccactt gtatttttt      1740 ttacaatgaa gcacccgtcc gcgtccgtgg acactgcaag tgcattgcca aaaaaaaaa      1800 aaaaaaaaa aaaaa                                                      1815
```

<210> SEQ ID NO 10
<211> LENGTH: 515
<212> TYPE: PRT
<213> ORGANISM: Zea mays
<220> FEATURE:
<223> OTHER INFORMATION: Mlo6

<400> SEQUENCE: 10

```
Met Gly Gly Gly Gly Gly Gly Asn Ser Arg Glu Leu Asp Gln Thr
  1               5                  10                  15

Pro Thr Trp Ala Val Ala Ser Val Cys Gly Val Ile Val Leu Ile Ser
             20                  25                  30

Ile Leu Leu Glu Lys Gly Leu His His Val Gly Glu Phe Phe Ser His
         35                  40                  45

Arg Lys Lys Lys Ala Met Val Glu Ala Leu Glu Lys Val Lys Ala Glu
     50                  55                  60

Leu Met Val Leu Gly Phe Ile Ser Leu Leu Val Phe Gly Gln Asn
 65                  70                  75                  80

Tyr Ile Ile Lys Val Cys Ile Ser Asn His Ala Ala Asn Thr Met Leu
                 85                  90                  95

Pro Cys Lys Leu Glu Ala Ala Ala Val Glu Gly Lys Asp Gly His Gly
            100                 105                 110

Lys Glu Ala Ala Ala Val Val Ala Gly Lys Lys Val Ala Val Ala
        115                 120                 125

Val Pro Gly Lys Lys Lys Lys Ala Ala Ala Ala Asp His Leu
    130                 135                 140

Gly Gly Val Val Asp Trp Pro Pro Tyr Tyr Ala His Asn Ala Arg
145                 150                 155                 160

Met Leu Ala Glu Ala Ser Met Ala Thr Lys Cys Pro Glu Gly Lys Val
                165                 170                 175

Pro Leu Ile Ser Ile Asn Ala Leu His Gln Leu His Ile Phe Ile Phe
            180                 185                 190

Phe Leu Ala Val Phe His Val Ser Tyr Ser Ala Ile Thr Met Ala Leu
```

-continued

```
            195                 200                 205
Gly Arg Ala Lys Ile Arg Ala Trp Lys Glu Trp Lys Glu Ala Ala
        210                 215                 220
Gly Gln Asp Tyr Glu Phe Ser His Asp Pro Thr Arg Phe Arg Phe Thr
225                 230                 235                 240
His Glu Thr Ser Phe Val Arg Gln His Met Asn Val Leu Asn Lys Phe
                245                 250                 255
Pro Ala Ser Phe Tyr Ile Ser Asn Phe Phe Arg Gln Phe Phe Arg Ser
                260                 265                 270
Val Arg Gln Ala Asp Tyr Cys Ala Leu Arg His Ser Phe Val Asn Val
            275                 280                 285
His Leu Ala Pro Gly Ser Lys Phe Asp Phe Gln Lys Tyr Ile Lys Arg
        290                 295                 300
Ser Leu Glu Asp Asp Phe Lys Val Ile Val Gly Ile Ser Pro Pro Leu
305                 310                 315                 320
Trp Ala Ser Ala Leu Ile Phe Leu Phe Leu Asn Val Asn Gly Trp His
                325                 330                 335
Thr Met Leu Trp Ile Ser Ile Met Pro Val Val Ile Ile Leu Ser Val
                340                 345                 350
Gly Thr Lys Leu Gln Gly Ile Ile Cys Arg Met Ala Ile Asp Ile Thr
            355                 360                 365
Glu Arg His Ala Val Ile Gln Gly Ile Pro Met Val Gln Val Ser Asp
        370                 375                 380
Ser Tyr Phe Trp Phe Ala Arg Pro Thr Phe Val Leu Phe Leu Ile His
385                 390                 395                 400
Phe Thr Leu Phe Gln Asn Gly Phe Gln Ile Ile Tyr Phe Leu Trp Ile
                405                 410                 415
Leu Tyr Glu Tyr Gly Met Asp Ser Cys Phe Asn Asp Ser Glu Glu Phe
                420                 425                 430
Val Phe Ala Arg Leu Cys Leu Gly Val Val Gln Val Leu Cys Ser
            435                 440                 445
Tyr Val Thr Leu Pro Leu Tyr Ala Leu Val Ser Gln Met Gly Ser Thr
        450                 455                 460
Met Lys Gln Ser Ile Phe Asp Glu Gln Thr Ser Lys Ala Leu Lys Asn
465                 470                 475                 480
Trp Arg Ala Gly Ala Lys Lys Lys Ala Pro Thr Gly Gly Ser Lys His
                485                 490                 495
Gly Gly Gly Gly Ser Pro Thr Ala Gly Gly Ser Pro Thr Lys Ala Asp
                500                 505                 510
Gly Asp Ala
        515
```

<210> SEQ ID NO 11
<211> LENGTH: 1660
<212> TYPE: DNA
<213> ORGANISM: Zea mays
<220> FEATURE:
<223> OTHER INFORMATION: Mlo7

<400> SEQUENCE: 11

| | | | | | |
|---|---|---|---|---|---|
| gctagcagga | gccaggtcgc | gccgacagca | gcagttggaa | gaggatccat | ggggaaggag | 60 |
| gcgacgcttg | cgttcacgcc | cacctgggtg | gtggccatcg | tatgcctcgt | catcgtctct | 120 |
| atctccctcg | ccgctgagcg | ctcactccat | tacctcggca | agtatctgga | gtgtaagaag | 180 |
| cagaaagcgc | ttttttcagc | tctacagaga | ctaaaagaag | agctaatgct | tctcggattc | 240 |

-continued

```
atttcattcg tcctgagtct ctcccaaggt tttattgtta gcatttgcat tccagaaact   300
tctactgact tcatgcttcc atgcaataga ggcaactcca gagttgcaga agaaggtgct   360
aaaatttgca acaaaaaggg tgatgttccc ttgctatcac tggaggcatt acatcagctg   420
cacattttca tatttgtact tggtttagtc catgttgtgt tctgcgctac aacaatatca   480
tttagtgggg ccaagatgag aaagtggaag cattgggaaa cagaaattca cagagaagta   540
catgagaagt tacagcaaga aaagaatgaa ggacaagggt catcattgag tattgttgtg   600
ctacatcggg agcaccagga tgaatttgtc cacaagcgga caagggatt ttggatgaag    660 ctcgctgttg caagctggat aactgcattc ttgaagcaat tcaagattc agtgagtaaa    720 tcagattatg aagcacttag atcagctttt gtcgtggaac actatcccga gaaccagat    780 attgatttcc acaaatacat gactcgcgct gttgaatatg agtttaaaag agttgttggt   840
atcagctggt atctgtggct ttttgtaatc ttattcctgc tgctgaatat aaatggatgg   900
cacacatact tctggttggc tttcttgcct ctatttctgt tacttattgt tggtgccaaa   960
ctagagcaca ttatcactcg gttggctcaa gaggcagcga tcattatc aaataataca   1020 gaggaagttc cgaaaataaa gccatgcaag gaccatttct ggtttcacaa gcctgagcta  1080
gtccttcatt tgatccattt catcctgttc cagaattcgt tcgagattag ttttttcttc   1140
tggattctgg tatcagaagg tttcggttcg tgtatgatgg aacggaagcc ttatgtcatt   1200
tccagacttg ttatcgggt gatcatcgaa gtcatctgca gctatatcac gctgccacta   1260
tacgccatcg tgacccatat gaccggacag atcaagctgc atggttttgg ctcccgcgtg   1320
cacgagagtg tccatggctg gatcggcttg aggaagaaac ccttctcgtt ctggaagatt   1380
cccggcggtg accctaacgc tgattccggc agggaggccg acgtaacccg cagggtggcc   1440
aaggagcggt cggggagctc gcgcagcatg ccgatggcgc cggctgacga gatcgtcacc   1500
gtcgacgacg tcgcggtggc tgcagctgcc gttggccaag gaccataaaa ttcctagcta   1560
gcaaacacca gcagggaagg caggcaggct gccgaggtac cgtgcgcagc gggttgatgg   1620
gtcggacgct gcggaaaatt cctcgtgtcg ggagcaggct                         1660
```

<210> SEQ ID NO 12
<211> LENGTH: 499
<212> TYPE: PRT
<213> ORGANISM: Zea mays
<220> FEATURE:
<223> OTHER INFORMATION: Mlo7

<400> SEQUENCE: 12

```
Met Gly Lys Glu Ala Thr Leu Ala Phe Thr Pro Thr Trp Val Val Ala
 1               5                  10                  15

Ile Val Cys Leu Val Ile Val Ser Ile Ser Leu Ala Ala Glu Arg Ser
            20                  25                  30

Leu His Tyr Leu Gly Lys Tyr Leu Glu Cys Lys Lys Gln Lys Ala Leu
        35                  40                  45

Phe Ser Ala Leu Gln Arg Leu Lys Glu Glu Leu Met Leu Leu Gly Phe
    50                  55                  60

Ile Ser Phe Val Leu Ser Leu Ser Gln Gly Phe Ile Val Ser Ile Cys
65                  70                  75                  80

Ile Pro Glu Thr Ser Thr Asp Phe Met Leu Pro Cys Asn Arg Gly Asn
                85                  90                  95

Ser Arg Val Ala Glu Glu Gly Ala Lys Ile Cys Asn Lys Lys Gly Asp
            100                 105                 110
```

```
Val Pro Leu Leu Ser Leu Glu Ala Leu His Gln Leu His Ile Phe Ile
        115                 120                 125
Phe Val Leu Gly Leu Val His Val Val Phe Cys Ala Thr Thr Ile Ser
    130                 135                 140
Phe Ser Gly Ala Lys Met Arg Lys Trp Lys His Trp Glu Thr Glu Ile
145                 150                 155                 160
His Arg Glu Val His Glu Lys Leu Gln Gln Glu Lys Asn Glu Gly Gln
                165                 170                 175
Gly Ser Ser Leu Ser Ile Val Val Leu His Arg Glu His Gln Asp Glu
            180                 185                 190
Phe Val His Lys Arg Thr Lys Gly Phe Trp Met Lys Leu Ala Val Ala
        195                 200                 205
Ser Trp Ile Thr Ala Phe Leu Lys Gln Phe Gln Asp Ser Val Ser Lys
    210                 215                 220
Ser Asp Tyr Glu Ala Leu Arg Ser Ala Phe Val Val Glu His Tyr Pro
225                 230                 235                 240
Glu Lys Pro Asp Ile Asp Phe His Lys Tyr Met Thr Arg Ala Val Glu
                245                 250                 255
Tyr Glu Phe Lys Arg Val Val Gly Ile Ser Trp Tyr Leu Trp Leu Phe
            260                 265                 270
Val Ile Leu Phe Leu Leu Leu Asn Ile Asn Gly Trp His Thr Tyr Phe
        275                 280                 285
Trp Leu Ala Phe Leu Pro Leu Phe Leu Leu Ile Val Gly Ala Lys
    290                 295                 300
Leu Glu His Ile Ile Thr Arg Leu Ala Gln Glu Ala Ala Ile Ser Leu
305                 310                 315                 320
Ser Asn Asn Thr Glu Glu Val Pro Lys Ile Lys Pro Cys Lys Asp His
                325                 330                 335
Phe Trp Phe His Lys Pro Glu Leu Val Leu His Leu Ile His Phe Ile
            340                 345                 350
Leu Phe Gln Asn Ser Phe Glu Ile Ser Phe Phe Trp Ile Leu Val
        355                 360                 365
Ser Glu Gly Phe Gly Ser Cys Met Met Glu Arg Lys Pro Tyr Val Ile
370                 375                 380
Ser Arg Leu Val Ile Gly Val Ile Ile Glu Val Ile Cys Ser Tyr Ile
385                 390                 395                 400
Thr Leu Pro Leu Tyr Ala Ile Val Thr His Met Thr Gly Gln Ile Lys
                405                 410                 415
Leu His Gly Phe Gly Ser Arg Val His Glu Ser Val His Gly Trp Ile
            420                 425                 430
Gly Leu Arg Lys Lys Pro Phe Ser Phe Trp Lys Ile Pro Gly Gly Asp
        435                 440                 445
Pro Asn Ala Asp Ser Gly Arg Glu Ala Asp Val Thr Arg Arg Val Ala
    450                 455                 460
Lys Glu Arg Ser Gly Ser Ser Arg Ser Met Pro Met Ala Pro Ala Asp
465                 470                 475                 480
Glu Ile Val Thr Val Asp Asp Val Ala Val Ala Ala Ala Val Gly
                485                 490                 495
Gln Gly Pro

<210> SEQ ID NO 13
<211> LENGTH: 1798
<212> TYPE: DNA
```

<210> ORGANISM: Zea mays
<220> FEATURE:
<223> OTHER INFORMATION: Mlo8

<400> SEQUENCE: 13

```
ccgggagcgg caagactggg acacgccagc cctttatttc gagctttctg cgtgcgggag      60
gggggttgac aggcgatggc ggccgagggc gaggcggcgg cgctggagtt cacaccgacg     120
tggatcgtcg cggcggtctg ctctctcatc gtgctcctct cgctcgtcgc cgagcgatgc     180
ctccactacc tcggcaagac gctcaagagg aagaaccaga agccgctctt cgaggcgctg     240
ctcaaggtca agaagagtt gatgcttctg gggttcatct ccctgctgct gacggtgttc     300
cagggatga tccggaggac gtgcatccct gaacgctgga cattccacat gctgccatgc     360
gagaagccag atgagaaggc cggtgaggcc gccaccatgg agcattttgt agggacgctt     420
ggcaggatcg gtaggcgtct gttgcaggaa ggcactgctg gggctgagca atgccagaag     480
aagggaaaag ttccactttt gtcccttgaa gccatacatc agctgcacat tttcatattt     540
gttctggcaa tcacacatgt tattttcagc gtcacaacta tgcttttagg aggtgcacag     600
atacaccaat ggaaacagtg ggagaatgga attaaaaaag atgctcctgg aaatgggcct     660
aaggtaacca atgtacatca tcatgaattt atcaagaaac gttttaaggg tattggcaaa     720
gattctataa tattgagttg gctgcattct tttggtaagc agttttatag atcagtatct     780
aaatcagatt acaccacaat gcgtcttggt tttatcatga ctcactgccc tggaaatcca     840
aaatttgatt tccatagata catggtaagg gttttagagg cggattttaa gaaagtggta     900
ggcataagct ggtacttgtg ggtcttcgtg gtgatatttc tgttgctgaa tgttaatggc     960
tggcacacat acttttggat tgctttcctt ccccttattc ttctgttagc cattggcact    1020
aagctggagc atgtcatagc tcagctagcc catgatgtag ctgagaagca cacagcggtc    1080
gagggcgatg tgatcgtaaa accatcagat gaacacttct ggttcggcaa gcctagggtt    1140
atcctttacc tgatccactt catcctcttt cagaatgcgt ttgagattgc gttttcttc    1200
tggatactga gcacttatgg attcgactcg tgcatcatgg acaagttcg tttttattgtg    1260
ccaaggcttg tcatcggggt ggttattcag cttctctgca gctacagcac cttgcctctg    1320
tatgcaattg taacccagat ggggagctgc tacaagaagg agatcttcaa cgagcatgtg    1380
cagcagggcg tcctgggctg ggctcagaag gtcaagatga aaaagggact gaagggagct    1440
gcatctgcta gcaaggacga atcgattacc aatgccgatt cggcaggacc ttccgttaag    1500
attgaaatgg cgaaggctgg ggaggatgtt gagatcgttg gaaacacagg ttgattggga    1560
caataggtg cccgtgttgt aatgatgtaa caggttaata tgccatcatc tttttttgta    1620
gatactagat agcttgctgt ggcaataccg caatagcggt gaactagaga aggtgagttt    1680
gggcccggga gcctcatctg ttatcggtcc agtaggaagc aaattcttat atacgggata    1740
tcgataagaa atgaactaag aacatgttcc tggattcatt aaaaaaaaaa aaaaaaa     1798
```

<210> SEQ ID NO 14
<211> LENGTH: 492
<212> TYPE: PRT
<213> ORGANISM: Zea mays
<220> FEATURE:
<223> OTHER INFORMATION: Mlo8

<400> SEQUENCE: 14

```
Met Ala Ala Glu Gly Glu Ala Ala Ala Leu Glu Phe Thr Pro Thr Trp
  1               5                  10                  15
```

```
Ile Val Ala Ala Val Cys Ser Leu Ile Val Leu Leu Ser Leu Val Ala
             20                  25                  30

Glu Arg Cys Leu His Tyr Leu Gly Lys Thr Leu Lys Arg Lys Asn Gln
         35                  40                  45

Lys Pro Leu Phe Glu Ala Leu Leu Lys Val Lys Glu Glu Leu Met Leu
     50                  55                  60

Leu Gly Phe Ile Ser Leu Leu Thr Val Phe Gln Gly Met Ile Arg
 65                  70                  75                  80

Arg Thr Cys Ile Pro Glu Arg Trp Thr Phe His Met Leu Pro Cys Glu
                 85                  90                  95

Lys Pro Asp Glu Lys Ala Gly Glu Ala Ala Thr Met Glu His Phe Val
             100                 105                 110

Gly Thr Leu Gly Arg Ile Gly Arg Arg Leu Leu Gln Glu Gly Thr Ala
         115                 120                 125

Gly Ala Glu Gln Cys Gln Lys Lys Gly Lys Val Pro Leu Leu Ser Leu
     130                 135                 140

Glu Ala Ile His Gln Leu His Ile Phe Ile Phe Val Leu Ala Ile Thr
145                 150                 155                 160

His Val Ile Phe Ser Val Thr Thr Met Leu Leu Gly Gly Ala Gln Ile
                 165                 170                 175

His Gln Trp Lys Gln Trp Glu Asn Gly Ile Lys Lys Asp Ala Pro Gly
             180                 185                 190

Asn Gly Pro Lys Val Thr Asn Val His His Glu Phe Ile Lys Lys
         195                 200                 205

Arg Phe Lys Gly Ile Gly Lys Asp Ser Ile Ile Leu Ser Trp Leu His
     210                 215                 220

Ser Phe Gly Lys Gln Phe Tyr Arg Ser Val Ser Lys Ser Asp Tyr Thr
225                 230                 235                 240

Thr Met Arg Leu Gly Phe Ile Met Thr His Cys Pro Gly Asn Pro Lys
                 245                 250                 255

Phe Asp Phe His Arg Tyr Met Val Arg Val Leu Glu Ala Asp Phe Lys
             260                 265                 270

Lys Val Val Gly Ile Ser Trp Tyr Leu Trp Val Phe Val Ile Phe
         275                 280                 285

Leu Leu Leu Asn Val Asn Gly Trp His Thr Tyr Phe Trp Ile Ala Phe
     290                 295                 300

Leu Pro Leu Ile Leu Leu Ala Ile Gly Thr Lys Leu Glu His Val
305                 310                 315                 320

Ile Ala Gln Leu Ala His Asp Val Ala Glu Lys His Thr Ala Val Glu
                 325                 330                 335

Gly Asp Val Ile Val Lys Pro Ser Asp Glu His Phe Trp Phe Gly Lys
             340                 345                 350

Pro Arg Val Ile Leu Tyr Leu Ile His Phe Ile Leu Phe Gln Asn Ala
         355                 360                 365

Phe Glu Ile Ala Phe Phe Trp Ile Leu Ser Thr Tyr Gly Phe Asp
     370                 375                 380

Ser Cys Ile Met Gly Gln Val Arg Phe Ile Val Pro Arg Leu Val Ile
385                 390                 395                 400

Gly Val Val Ile Gln Leu Leu Cys Ser Tyr Ser Thr Leu Pro Leu Tyr
                 405                 410                 415

Ala Ile Val Thr Gln Met Gly Ser Cys Tyr Lys Lys Glu Ile Phe Asn
             420                 425                 430

Glu His Val Gln Gln Gly Val Leu Gly Trp Ala Gln Lys Val Lys Met
```

```
                435              440              445
Lys Lys Gly Leu Lys Gly Ala Ala Ser Ala Ser Lys Asp Glu Ser Ile
            450              455              460
Thr Asn Ala Asp Ser Ala Gly Pro Ser Val Lys Ile Glu Met Ala Lys
465              470              475              480
Ala Gly Glu Asp Val Glu Ile Val Gly Asn Thr Gly
                485              490
```

<210> SEQ ID NO 15
<211> LENGTH: 1557
<212> TYPE: DNA
<213> ORGANISM: Zea mays
<220> FEATURE:
<223> OTHER INFORMATION: Mlo9

<400> SEQUENCE: 15

| | | | | | |
|---|---|---|---|---|---|
| cattcaccga | ggagaaatct | gaaaactagt | taccataacc | atgaaggctg | ccgtgaggga | 60 |
| tatgagtcat | ttgtttcgca | tgaaggtttg | gagcagctgc | accggtttat | atttgtaatg | 120 |
| gctgtgactc | atgtgactta | tagctgcctg | acgatgttac | tagcaatact | caagatccat | 180 |
| aaatggagaa | aatgggagga | tgaagcattc | agggataatc | atgaatcatt | ttctcagatc | 240 |
| gcatatgagt | cagcaactag | aaggcaacca | gcacttacca | aatcctattc | attccgctct | 300 |
| tggagccaaa | ataatgtggt | catgtggctt | gtttgcttta | ttgcgcaatt | tggtcagtct | 360 |
| gttgttcgag | cagactatct | tatcctccgc | aagggtttta | taatgaccca | caatcttccg | 420 |
| ccaacatatg | atttccacaa | ttacatgata | cgctcaatgg | aagaggagtt | tgagaagatt | 480 |
| gtcggagtga | gtggactgtt | gtggggcttc | gttgttgctt | ttatgttatt | taatgtagac | 540 |
| ggatccaacc | tgtactttg | gatagcaatt | cttcctgtaa | ctcttgttct | tctggtgggt | 600 |
| gcaaagctgc | agcatgtgat | tgcgactcta | acagcagagg | gcgcaaagat | gagcacctac | 660 |
| gggccaagga | tacagccaag | ggatgatctc | ttttggttca | agaaaccaga | gtttctcctt | 720 |
| tggttgatac | acttcgttct | ctttcagaat | gccttcgagt | tggcttcgtt | cttctggttc | 780 |
| tggtggcaat | ttggttatga | ttcatgcttc | atcaaaaacc | accttttggt | atattgccgc | 840 |
| cttatactgg | ggtttgctgg | acagttcctg | tgcagttaca | gtacattacc | tgtatatgcg | 900 |
| ctggtcactc | agatggggtc | caagtacaag | gctgcgctga | tcccgcggag | gatcaggag | 960 |
| accatacatg | ggtggggaaa | agcgacgagg | aagaagcgcc | ggcgccgccg | cggcgacgac | 1020 |
| tcgacggtcc | gcacggagac | gagcacggtg | tgctcgctca | cggacgacga | cgaagacttc | 1080 |
| gaagacgacg | acgaccacca | ccaccacgga | ccgtcgtacg | ataccccgag | agccggggc | 1140 |
| cgcccgccgt | acctgaagat | cgagacgcat | cgtcagtcgg | gcagcgggca | cgacggcccc | 1200 |
| aggcccggcg | gcaccccgtg | cttccacccc | agcggcagcg | gcagcgggca | cgccatgctc | 1260 |
| ctgcggcagg | cctccgtctc | cgcgccgtcg | tcgccgtcgt | accgcggagg | caataacgtg | 1320 |
| acaaggtcgg | cgtccatgcc | cggatcgcc | gcgctgagga | caacgggctc | cggcacgccg | 1380 |
| acgcgcgtga | gccatgagga | gcctacttga | tgcgcgcccg | tgcatgccat | ggatggcttg | 1440 |
| ctagtgcaga | cgtactgagg | actgagctgc | tagtgtagca | ccggatttga | aggtatatcg | 1500 |
| atatatatat | acacacgaaa | agatttgggg | tgacaaaaaa | aaaaaaaaaa | aaaaaaa | 1557 |

<210> SEQ ID NO 16
<211> LENGTH: 469
<212> TYPE: PRT
<213> ORGANISM: Zea mays
<220> FEATURE:

-continued

<223> OTHER INFORMATION: Mlo9

<400> SEQUENCE: 16

```
His Ser Pro Arg Arg Asn Leu Lys Thr Ser Tyr His Asn His Glu Gly
 1               5                  10                  15

Cys Arg Glu Gly Tyr Glu Ser Phe Val Ser His Glu Gly Leu Glu Gln
             20                  25                  30

Leu His Arg Phe Ile Phe Val Met Ala Val Thr His Val Thr Tyr Ser
         35                  40                  45

Cys Leu Thr Met Leu Leu Ala Ile Leu Lys Ile His Lys Trp Arg Lys
 50                  55                  60

Trp Glu Asp Glu Ala Phe Arg Asp Asn His Glu Ser Phe Ser Gln Ile
 65                  70                  75                  80

Ala Tyr Glu Ser Ala Thr Arg Arg Gln Pro Ala Leu Thr Lys Ser Tyr
                 85                  90                  95

Ser Phe Arg Ser Trp Ser Gln Asn Val Val Met Trp Leu Val Cys
            100                 105                 110

Phe Ile Ala Gln Phe Gly Gln Ser Val Val Arg Ala Asp Tyr Leu Ile
        115                 120                 125

Leu Arg Lys Gly Phe Ile Met Thr His Asn Leu Pro Pro Thr Tyr Asp
    130                 135                 140

Phe His Asn Tyr Met Ile Arg Ser Met Glu Glu Glu Phe Glu Lys Ile
145                 150                 155                 160

Val Gly Val Ser Gly Leu Leu Trp Gly Phe Val Val Ala Phe Met Leu
                165                 170                 175

Phe Asn Val Asp Gly Ser Asn Leu Tyr Phe Trp Ile Ala Ile Leu Pro
            180                 185                 190

Val Thr Leu Val Leu Leu Val Gly Ala Lys Leu Gln His Val Ile Ala
        195                 200                 205

Thr Leu Thr Ala Glu Gly Ala Lys Met Ser Thr Tyr Gly Pro Arg Ile
    210                 215                 220

Gln Pro Arg Asp Asp Leu Phe Trp Phe Lys Lys Pro Glu Phe Leu Leu
225                 230                 235                 240

Trp Leu Ile His Phe Val Leu Phe Gln Asn Ala Phe Glu Leu Ala Ser
                245                 250                 255

Phe Phe Trp Phe Trp Trp Gln Phe Gly Tyr Asp Ser Cys Phe Ile Lys
            260                 265                 270

Asn His Leu Leu Val Tyr Cys Arg Leu Ile Leu Gly Phe Ala Gly Gln
        275                 280                 285

Phe Leu Cys Ser Tyr Ser Thr Leu Pro Val Tyr Ala Leu Val Thr Gln
    290                 295                 300

Met Gly Ser Lys Tyr Lys Ala Ala Leu Ile Pro Arg Ile Arg Glu
305                 310                 315                 320

Thr Ile His Gly Trp Gly Lys Ala Thr Arg Lys Arg Arg Arg Arg
                325                 330                 335

Arg Gly Asp Asp Ser Thr Val Arg Thr Glu Thr Ser Thr Val Cys Ser
            340                 345                 350

Leu Thr Asp Asp Asp Glu Asp Phe Glu Asp Asp Asp His His His
    355                 360                 365

His Gly Pro Ser Tyr Asp Thr Pro Arg Ala Gly Arg Pro Pro Tyr
370                 375                 380

Leu Lys Ile Glu Thr His Arg Gln Ser Gly Ser Gly His Asp Gly Pro
385                 390                 395                 400
```

-continued

```
Arg Pro Gly Gly Thr Pro Cys Phe His Pro Ser Gly Ser Gly
                405                 410                 415

His Ala Met Leu Leu Arg Gln Ala Ser Val Ser Ala Pro Ser Ser Pro
            420                 425                 430

Ser Tyr Arg Gly Gly Asn Asn Val Thr Arg Ser Ala Ser Met Pro Gly
            435                 440                 445

Ile Ala Ala Leu Arg Thr Thr Gly Ser Gly Thr Pro Thr Arg Val Ser
    450                 455                 460

His Glu Glu Pro Thr
465

<210> SEQ ID NO 17
<211> LENGTH: 533
<212> TYPE: PRT
<213> ORGANISM: Hordeum vulgare

<400> SEQUENCE: 17

Met Ser Asp Lys Lys Gly Val Pro Ala Arg Glu Leu Pro Glu Thr Pro
1               5                   10                  15

Ser Trp Ala Val Ala Val Val Phe Ala Ala Met Val Leu Val Ser Val
            20                  25                  30

Leu Met Glu His Gly Leu His Lys Leu Gly His Trp Phe Gln His Arg
        35                  40                  45

His Lys Lys Ala Leu Trp Glu Ala Leu Glu Lys Met Lys Ala Glu Leu
    50                  55                  60

Met Leu Val Gly Phe Ile Ser Leu Leu Leu Ile Val Thr Gln Asp Pro
65                  70                  75                  80

Ile Ile Ala Lys Ile Cys Ile Ser Glu Asp Ala Ala Asp Val Met Trp
                85                  90                  95

Pro Cys Lys Arg Gly Thr Glu Gly Arg Lys Pro Ser Lys Tyr Val Asp
            100                 105                 110

Tyr Cys Pro Glu Gly Lys Val Ala Leu Met Ser Thr Gly Ser Leu His
        115                 120                 125

Gln Leu His Val Phe Ile Phe Val Leu Ala Val Phe His Val Thr Tyr
    130                 135                 140

Ser Val Ile Thr Ile Ala Leu Ser Arg Leu Lys Met Arg Thr Trp Lys
145                 150                 155                 160

Lys Trp Glu Thr Glu Thr Thr Ser Leu Glu Tyr Gln Phe Ala Asn Asp
                165                 170                 175

Pro Ala Arg Phe Arg Phe Thr His Gln Thr Ser Phe Val Lys Arg His
            180                 185                 190

Leu Gly Leu Ser Ser Thr Pro Gly Ile Arg Trp Val Val Ala Phe Phe
        195                 200                 205

Arg Gln Phe Phe Arg Ser Val Thr Lys Val Asp Tyr Leu Thr Leu Arg
    210                 215                 220

Ala Gly Phe Ile Asn Ala His Leu Ser Gln Asn Ser Lys Phe Asp Phe
225                 230                 235                 240

His Lys Tyr Ile Lys Arg Ser Met Glu Asp Asp Phe Lys Val Val Val
                245                 250                 255

Gly Ile Ser Leu Pro Leu Trp Gly Val Ala Ile Leu Thr Leu Phe Leu
            260                 265                 270

Asp Ile Asn Gly Val Gly Thr Leu Ile Trp Ile Ser Phe Ile Pro Leu
        275                 280                 285

Val Ile Leu Leu Cys Val Gly Thr Lys Leu Glu Met Ile Ile Met Glu
    290                 295                 300
```

```
Met Ala Leu Glu Ile Gln Asp Arg Ala Ser Val Ile Lys Gly Ala Pro
305                 310                 315                 320

Val Val Glu Pro Ser Asn Lys Phe Phe Trp Phe His Arg Pro Asp Trp
            325                 330                 335

Val Leu Phe Phe Ile His Leu Thr Leu Phe Gln Asn Ala Phe Gln Met
            340                 345                 350

Ala His Phe Val Trp Thr Val Ala Thr Pro Gly Leu Lys Lys Cys Tyr
            355                 360                 365

His Thr Gln Ile Gly Leu Ser Ile Met Lys Val Val Gly Leu Ala
370                 375                 380

Leu Gln Phe Leu Cys Ser Tyr Met Thr Phe Pro Leu Tyr Ala Leu Val
385                 390                 395                 400

Thr Gln Met Gly Ser Asn Met Lys Arg Ser Ile Phe Asp Glu Gln Thr
                405                 410                 415

Ser Lys Ala Leu Thr Asn Trp Arg Asn Thr Ala Lys Glu Lys Lys Lys
            420                 425                 430

Val Arg Asp Thr Asp Met Leu Met Ala Gln Met Ile Gly Asp Ala Thr
            435                 440                 445

Pro Ser Arg Gly Ser Ser Pro Met Pro Ser Arg Gly Ser Ser Pro Val
            450                 455                 460

His Leu Leu His Lys Gly Met Gly Arg Ser Asp Asp Pro Gln Ser Ala
465                 470                 475                 480

Pro Thr Ser Pro Arg Thr Gln Gln Glu Ala Arg Asp Met Tyr Pro Val
                485                 490                 495

Val Val Ala His Pro Val His Arg Leu Asn Pro Asn Asp Arg Arg Arg
            500                 505                 510

Ser Ala Ser Ser Ser Ala Leu Glu Ala Asp Ile Pro Ser Ala Asp Phe
            515                 520                 525

Ser Phe Ser Gln Gly
    530

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
agttatccaa ggcatgccgg tggtaaaact                                    30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
aagtcatcga gggaggcatc acttacag                                      28

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:
```

```
       oligonucleotide primer

<400> SEQUENCE: 20
agagaagcca acgccawcgc ctcyatttcg tc                                    32
```

MANIPULATION OF *MLO* GENES TO ENHANCE DISEASE RESISTANCE IN PLANTS

CROSS-REFERENCE

This application claims the benefit of U.S. Provisional Application No. 60/091,875, filed Jul. 7, 1998.

FIELD OF THE INVENTION

The invention relates to the genetic manipulation of plants, particularly to transforming plants with genes that enhance disease resistance.

BACKGROUND OF THE INVENTION

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism. This limitation of the pathogen intruder is frequently accomplished by localized containment of the intruder following a coordinated complex defense response.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

The hypersensitive response in many plant-pathogen interactions is specified by and dependent on the presence of two complementary genes, one from the host and one from the pathogen. These complementary genes are the resistance (R) gene in the plant and a corresponding avirulence (avr) gene in the pathogen. The interaction of the genes is associated with the rapid, localized cell death of the hypersensitive response. R genes that respond to specific bacterial, fungal, or viral pathogens, have been isolated from a variety of plant species and several appear to encode cytoplasmic proteins.

The resistance gene in the plant and the avirulence gene in the pathogen often conform to a gene-for-gene relationship. That is, resistance to a pathogen is only observed when the pathogen carries a specific avirulence gene and the plant carries a corresponding or complementing resistance gene. Because avr-R gene-for-gene relationships are observed in many plant-pathogen systems and are accompanied by a characteristic set of defense responses, a common molecular mechanism underlying avr-R gene mediated resistance has been postulated. A simple model which has been proposed is that pathogen avr genes directly or indirectly generate a specific molecular signal (ligand) that is recognized by cognate receptors encoded by plant R genes.

Both plant resistance genes and corresponding pathogen avirulence genes have been cloned. The plant kingdom contains thousands of R genes with specific specificities for viral, bacterial, fungal, or nematode pathogens. Although there are differences in the defense responses induced during different plant-pathogen interactions, some common themes are apparent among R gene-mediated defenses. The function of a given R gene is dependent on the genotype of the pathogen. Plant pathogens produce a diversity of potential signals, and in a fashion analogous to the production of antigens by mammalian pathogens, some of these signals are detectable by some plants.

The avirulence gene causes the pathogen to produce a signal that triggers a strong defense response in a plant with the appropriate R gene. However, expressing an avirulence gene does not stop the pathogen from being virulent on hosts that lack the corresponding R gene. A single plant can have many R genes, and a pathogen can have many avr genes.

Monogenic resistance mediated by recessive (mlo) alleles of the Mlo locus is different. It differs from race-specific incompatibility to single pathogen strains in that it is believed to confer a broad spectrum resistance to almost all known isolates of the fungal pathogen, and the resistance is apparently durable in the field despite extensive cultivation. Further, mlo resistance alleles have been obtained by mutagen treatment of susceptible wild-type Mlo varieties. These mlo plants exhibit a spontaneous leaf cell death phenotype under pathogen-free or even axenic conditions.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight.

Accordingly, molecular methods are needed to supplement traditional breeding methods to protect plants from pathogen attack. Particularly, methods are needed for broad spectrum resistance to pathogens.

SUMMARY OF THE INVENTION

Compositions and methods for creating or enhancing resistance to plant pests are provided. The method provides control of pathogens by modulating the expression of Mlo genes. Novel Mlo sequences are provided from maize. Such sequences can be utilized to modulate the expression of Mlo genes in plants, particularly maize, to enhance resistance to pathogens. Generally, such modulation will result in decreased or increased expression of native Mlo genes, preferably decreased expression. Such decreased expression can be effected by mutagenesis or expression of modified or antisense Mlo sequences described herein.

It is recognized that a variety of promoters will be useful in the invention the choice of which will depend in part upon the desired level of expression of the modified sequences in the plant or alternatively, in the plant organ. It is recognized that the levels of expression can be controlled to induce broad spectrum resistance resulting in levels of immunity in the plant or to induce cell death.

The methods of the invention find use in controlling plant pests, including fungal pathogens, viruses, nematodes, insects, and the like. Transformed plants and seeds, as well as methods for making such plants and seeds are additionally provided.

BRIEF DESCRIPTION OF THE DRAWINGS

FIG. 1 provides a sequence alignment for the maize Mlo homologues with the barley Mlo sequence. The barley sequence is designated as HvMlo1.

DETAILED DESCRIPTION OF THE INVENTION

Figure 2:
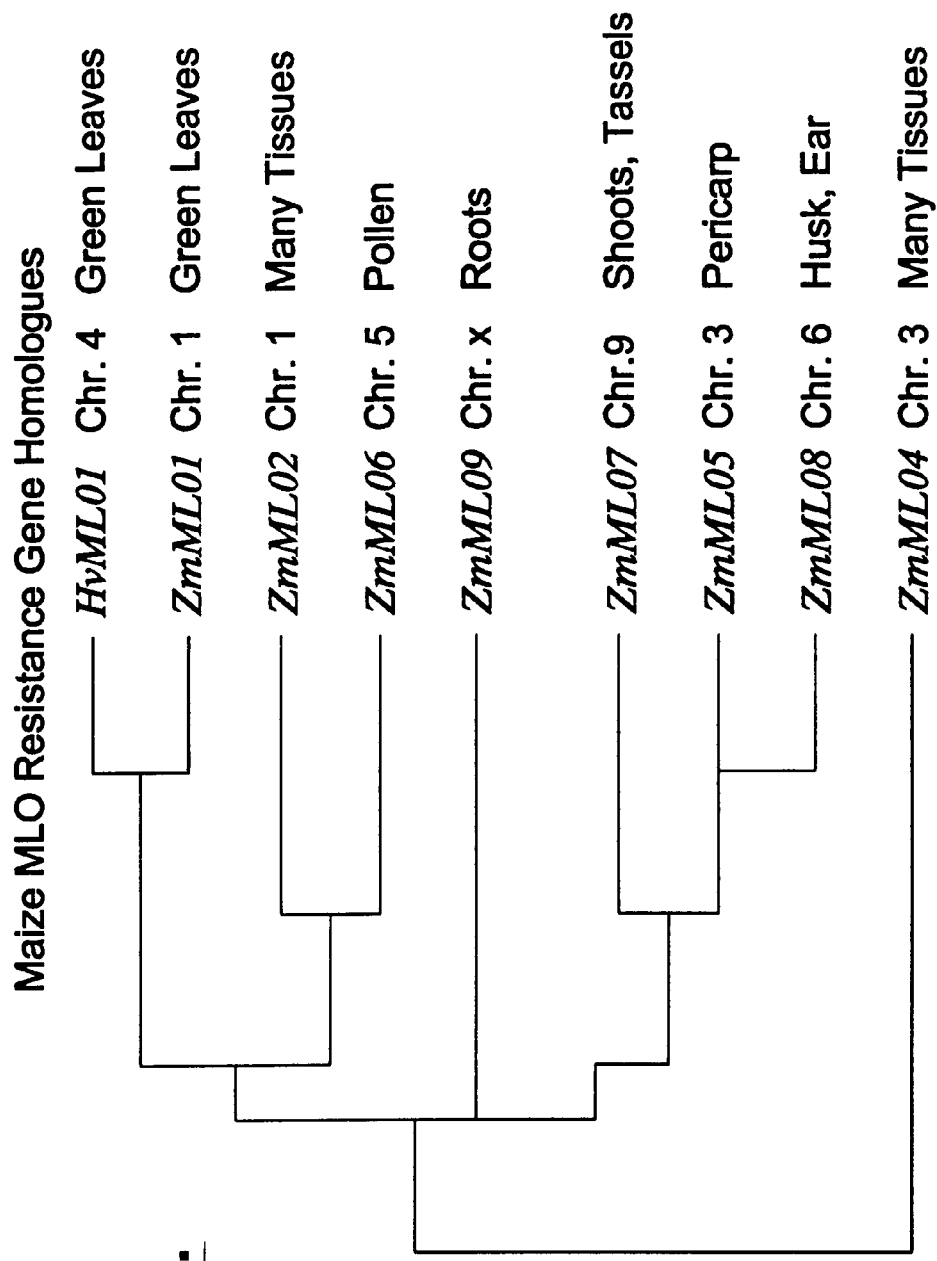
FIG. 2 groups the Mlo sequences based on relatedness as well as the plant tissue from which it was isolated.

Compositions of the invention include eight mutation-induced recessive alleles of maize set forth in SEQ ID NOS: 1, 3, 5, 7, 9, 11, 13 and 15. The maize sequences exhibit homology to the Mlo barley sequence (SEQ ID NO: 17). See, Büschges et al. (1997) 88:695–705 and Tables 1 and 2. The isolated maize Mlo genes are involved in enhancing resistance to plant pests. In particular, the present invention provides for isolated nucleic acid molecules comprising nucleotide sequences encoding the amino acid sequences shown in SEQ ID NOS: 2, 4, 6, 8, 10, 12, 14, 16, or the nucleotide sequences encoding the DNA sequences deposited in a bacterial host with the American Type Culture Collection and assigned the Accession Nos. 98725, 98726, 98727, 98728, 98729 (SEQ ID NOS: 3, 5, 9, 11, 13 respectively). Further provided are polypeptides having an amino acid sequence encoded by a nucleic acid molecule described herein, for example those set forth in SEQ ID NOS: 1, 5, 3, 7, 9, 11, 13, and 15, those deposited with the American Type Culture Collection and assigned Accession Nos. 98725, 98726, 98727, 98728, 98729 (SEQ ID NOS: 3, 5, 9, 11, 13 respectively), and fragments and variants thereof.

Plasmids containing the nucleotide sequences of the invention were deposited with American Type Culture Collection, Manassas, Va., and assigned Accession Nos. 98725, 98726, 98727, 98728, 98729 (SEQ ID NOS: 3, 5, 9, 11, 13 respectively). These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence their altered expression enhances resistance to pathogens. Alternatively, fragments of a nucleotide sequence that are useful as hybridization probes generally do not encode protein fragments retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Mlo nucleotide sequence that encodes a biologically active portion of a Mlo protein of the invention will encode at least 15, 20, 25, 30, 40, 50, 75, 100, 200, 250, 300, 350, 400, 450, 500, or 550 contiguous amino acids, or up to the total number of amino acids present in a full-length MLO protein of the invention. (For example, 509, 499, and 492, amino acids for SEQ ID NOS: 6, 12, and 14 respectively.) Fragments of a Mlo nucleotide sequence that are useful as hybridization probes for PCR primers generally need not encode a biologically active portion of a MLO protein.

Thus, a fragment of a Mlo nucleotide sequence may encode a biologically active portion of a MLO protein, or it may be a fragment that can be used as a hybridization probe or PCR primer using methods disclosed below. A biologically active portion of a MLO protein can be prepared by isolating a portion of one of the Mlo nucleotide sequences of the invention, expressing the encoded portion of the MLO protein (e.g., by recombinant expression in vitro), and assessing the activity of the encoded portion of the MLO protein. Nucleic acid molecules that are fragments of a Mlo nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, and 2,000 nucleotides, or up to the number of nucleotides present in a full-length Mlo nucleotide sequence disclosed herein.

By "variants" is intended substantially similar sequences. For nucleotide sequences, conservative variants include those sequences that, because of the degeneracy of the genetic code, encode the amino acid sequence of one of the MLO polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a MLO protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the Mlo proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ability to enhance resistance to pathogens when their expression is altered. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by an enhanced resistance to pathogens when the expression of the protein sequences is altered.

Variant nucleotide sequences and proteins also encompass sequences and proteins derived from a mutagenic and recombinogenic procedure such as DNA shuffling. With such a procedure, one or more different Mlo coding sequences can be manipulated to create a new Mlo coding sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Mlo gene of the invention and other known genes involved in pathogen resistance to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The maize Mlo homologues are associated with disease related loci as shown in Table 3. Mapping information of the sequences are given in Table 5. The maize homologue proteins are predicted to be membrane-anchored by at least six, and possibly seven membrane-spanning helices. The maize sequences find use in negative control function of the MLO protein in leaf cell death and in the onset of pathogen defense. Generally, the methods of the invention take advantage of the absence of MLO to prime responsiveness of the plant to disease.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire Mlo sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the Mlo sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire sequence of the Mlo nucleotide sequences disclosed herein, or one or more portions thereof, may be used as a probe capable of specifically hybridizing to corresponding Mlo sequences and messenger RNAs. To achieve specific hybridization under a variety of conditions, such probes include sequences that are unique among Mlo sequences and are preferably at least about 10 nucleotides in length, and most preferably at least about 20 nucleotides in length. Such probes may be used to amplify corresponding Mlo sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (% GC) $-0.61$ (% form) $-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode for a Mlo protein and hybridize to the Mlo sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. AppL. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention is drawn to methods for creating or enhancing resistance in a plant to plant pests by modulating the activity of Mlo genes in the plant. While the invention is not bound by any particular mechanism of action, it is believed that the methods of the invention will result in broad-based resistance in the modified plant. Accordingly, the methods are also useful in protecting plants against fungal pathogens, viruses, nematodes, insects and the like.

By "modulating activity" is intended that the expression of the Mlo gene is altered in some manner. Such modulation (increase or decrease) of expression results in enhanced resistance to pathogens. Generally, the methods of the invention will result in a decrease in the native protein or in protein activity. Thus, plants and plant cells are obtained having altered levels of MLO protein, preferably a decrease in protein levels. Such plants, plant cells and plant tissues are "modified" in that MLO protein levels are altered. As noted below, various methods are available for creating modified plants, plant cells and plant tissues including transformation and transfection leading to altered Mlo expression in the modified plant, plant cell or tissue.

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. insidiosum, *Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. alfalfae, *Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum I, II & III* (*Cochliobolus carbonum*), *Exserohilum turcicum I, II & III, Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. zea, *Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, lesion, and renniform nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; Helicoverpa zea, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; Helicoverpa zea, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; Helicoverpa zea, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; Helicoverpa zea, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis epsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The present invention exploits the use of Mlo genes. The Mlo sequences provided herein can be utilized to alter the expression of native Mlo genes in plants. The mlo mutation confers recessive resistance to pathogens. Broad spectrum resistance in plants can be enhanced by defective Mlo genes.

While the invention is not bound by any model, Mlo could have a negative control function in leaf cell death. In this model, Mlo would suppress a default cell suicide program in foliar tissue. Also, the MLO protein could have a specific negative regulatory function which works by down-regulating multiple disease-related functions. In this instance, spontaneous cell death in mlo mutant genotypes merely represents cell death because of accumulating activation of defense responses.

Several methods are available in the art for modulating the activity of Mlo genes. Mlo antisense sequences can be expressed in the plant cell. Such sequences will function to decrease expression of the maize Mlo genes as well as Mlo genes in other plants where the Mlo sequences share sequence identity.

It is recognized that with these nucleotide sequences, antisense constructions, complementary to at least a portion of the messenger RNA (mRNA) for the Mlo sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The antisense construct may be proximal to the 5'-terminus or capping site, downstream from the capping site, between the capping site and the initiation codon and may cover all or a portion of the non-coding region. Additionally, the sequence may bridge the non-coding and coding region, be complementary to all or part of the coding region, to the 3'-terminus of the coding region, or complementary to the 3'-untranslated region of the mRNA.

It is recognized that the particular site to which the antisense sequence binds and the length of the antisense sequence will vary depending upon the degree of inhibition desired, the uniqueness of the sequence, the stability of the antisense sequence, and the like. See, for example, U.S. Pat. Nos. 5,453,566; 5,530,192; and 5,728,926; all of which are herein incorporated by reference.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Individual Mlo genes or sets of Mlo genes can be rendered nonfunctional by mutagenesis. Such mutagenesis techniques include transposon disruption and recovery of such disruptions by reverse genetics approaches. Likewise, transformation-mediated mutagenesis may be utilized.

Disruption may be accomplished by transformation with gene replacement or gene truncation-disruption. See, for example, Bowen et al. (1995) *Mol. Gen. Gent.* 246:196–205; Walz et al. (1993) *Curr. Gent.* 25:421–427; Sweigard et al. (1992) *Mol. Gen. Gent.* 232:183–190; Hohn and Desjardins (1992) *Mol. Plant Microbe Interact* 5:249–256; Weber and Laitner (1994) *Curr. Gent.* 26:461–467; Templeton et al. (1994) *Gene* 142:141–146; Gorlach et al. (1998) *Appl. Environ. Microbiol.* 64:385–391; Schaeffer et al. (1994) *Appl. Environ. Microbiol.* 60:594–598; and the like, herein incorporated by reference. See also, Kempin et al. (1997) *Nature* 389:802–803 and Koncz et al. (1992) *Plant Mol. Biol.* 20:963–976.

Alternatively, the naturally occurring Mlo sequence or sequences may be modified by site-directed mutagenesis. Such methods may be utilized to induce specific alterations in targeted genes. One means for site-directed mutagenesis includes targeting modification or mutation of the Mlo sequences by homologous recombination. The method involves the use of RNA-DNA hybrid oligonucleotides. Such nucleotides exploit the natural recombinogenicity of RNA-DNA hybrids. The oligonucleotides are duplex oligonucleotides that share homology with at least one Mlo sequence. While any region of the Mlo sequence can be targeted, it may be preferable to target the 5' region of the Mlo sequence. See, for example, U.S. Pat. No, 5,565,350 that describes chimeric oligonucleotides useful for targeted gene correction for use in cultured mammalian cells; as well as U.S. provisional application Serial No. 06/065,628 drawn to gene manipulation in plant cells, herein incorporated by reference. Such methods can be used to alter or disrupt the ATG start codon for the gene.

Alternatively, protein coding regions of Mlo genes can be altered in such a manner that the gene products or proteins perform their function in a dominant negative manner resulting in a resistant phenotype. See, for example Krylov et al. (1997) *Proc. Natl. Acad. Sci. USA* 94:12274–12279.

Where the method of the invention relies upon the expression of an altered Mlo sequence or an Mlo antisense sequence in a plant, a number of promoters can be used. The promoters can be selected from constitutive and/or inducible promoters. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. See, also copending application entitled "Inducible Maize promoters", filed and herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93:14972–14977. See also, Chen et al. (1996) *Plant J.* 10:955–966; Zhang and Sing (1994) *Proc. Natl Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

Constitutive promoters include, for example, the core promoter of the Rsyn7 (copending application Ser. No. 08/661,601), the 35S promoter, the core 35S promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. See also, copending application entitled "Constitutive Maize Promoters" Provisional Application Serial No. 60/076,075 filed Feb. 26, 1998, and herein incorporated by reference.

Tissue specific promoters include Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell. Differ.* 20:181–196; Orozco et al. (1993) *Plant Mol. Biol.* 23(6): 1129–1138; Matsuoka et al. (1993) *Proc. Natl. Acad. Sci. U.S.A.* 90(20):9586–9590; and Guevara-Garcia et al. (1993) *Plant J.* 4(3):495–505.

The methods of the invention can be used with other methods for increasing pathogen resistance in plants. See, for example, Cai et al. (1997) *Science* 275:832–834; Roberts and Gallum (1984) *J. Heredity* 75:147–148; Ryerson and Heath (1996) *Plant Cell* 8:393–402 and Dangl et al. (1996) *Plant Cell* 8:1793–1807.

Altered Mlo sequences or antisense Mlo sequences of the invention can be introduced into any plant. The sequences to be introduced may be used in expression cassettes for expression in any plant of interest where expression in the plant cell is necessary. In other instances, such as for recombination, oligonucleotides are synthesized, purified and introduced into the plant cell.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of a MLO protein in the plant or plant cell. Thus, the phenotype of the plant or plant cell is altered.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

Nucleotide sequences of the invention are provided in expression cassettes for expression in the plant of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad Sci. USA* 85:43054309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of*

*Botany* 75:407–413 (rice); Osjoda et al. (1996) *Nature Biotechnology* 14:745–750 (maize via Agrobacterium tumefaciens); all of which are herein incorporated by reference.

The modified plant may be grown into plants in accordance with conventional ways. See, for example, McCormick et al. (1986) *Plant Cell. Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The Mlo sequences of the invention are also useful as molecular markers. Such markers are useful in breeding programs, particularly those aimed at improving disease resistance. The maize Mlo sequences have been mapped to chromosome locations and these positions related to known disease resistance loci.

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson (1996) (Chapter 2) in: Genome Mapping in Plants (ed. Andrew H. Paterson) by Academic Press/R. G. Landis Company, Austin, Texas, pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (Cm), often within 40 or 30 Cm, preferably within 20 or 10 Cm, more preferably within 5, 3, 2, or 1 Cm of a gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or PstI genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single-stranded conformation analysis (SSCP); 2) denaturing gradient gel electrophoresis (DGGE); 3) Rnase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The following examples are offered by way of illustration and not by way of limitation.

EXPERIMENTAL

Mlo Sequences

Eight maize Mlo homologue sequences have been identified. The nucleotide sequences (SEQ ID NOS: 1, 3, 5, 7, 9, 11, 13, and 15) and amino acid sequences (SEQ ID NOS: 2, 4, 6, 8, 10, 12, 14, and 16) are provided. DNA sequence analysis was performed according to Sambrook et al. (1989) *Mol. Cloning: A Laboratory Manual*, 2nd ed. (Cold Spring Harbor Laboratory Press, Plainview, N.Y.). The maize Mlo homologue/orthologue cDNA sequences were identified from mRNA isolated from various maize tissues and used to make cDNAs that are then cloned into vectors, usually pSPORT1. These cDNA libraries are EST sequenced via standard dye-fluorescence labeling and ABI machine electrophoresis and image capture. The Mlo homologues were identified by their blast score identity to the barley HvMLO1 published sequence. These maize clones, in particular the longest members of each contig or gene, were obtained and additional sequencing was done on them using oligonucleotide primers designed to internal portions of the cDNA and dye-fluorescence labeling and ABI machine electrophoresis and image capture. The complete edited sequences were assembled and analyzed.

The sequences from maize show sequence similarity to the published barley Mlo sequence as provided in Tables 1 and 2. FIG. 1 provides a sequence alignment for the maize Mlo homologues with the barley Mlo sequence designated as HvMlo1. FIG. 2 groups the Mlo sequences based on relatedness as well as the plant tissue from which it was isolated.

The ZmMLO genes were mapped by RFLP analysis using Southern blots of genomic DNA isolated from F2 and F3 and F4 segregating maize populations. The DNA was isolated using a modified CTAB adapted from the CERES RFLP Lab Manuel based on the Saghai-Mahoof procedure (Saghai-Mahoof et al. (1984) *Proc. Natl. Acad. Sci. USA* 81:8014–8018). Genomic DNA was cut with four restriction enzymes BamHI, EcoRI, EcoRV, and HindIII and run (5 μg/lane) on 0.8% TAE agarose gels for 800 volt-hours. The gels were Southern blot transferred to Hybond-N membrane (Amersham Life Science), baked and UV-crosslinked. The ZmMLO cDNA inserts were liberated from its vector by cleaving with two restriction enzymes, usually SalI and NotI, and the insert was purified from agarose gels following electrophoresis. The clone was random prime labeled with $^{32}$P-dCTP using the RTS (Gibco BRL) labeling kit. The cDNA inserts were used to probe parental screening blots to identify a mapping population with a RFLP polymorphism. Once a polymorphism was identified, the inserts were used to probe mapping blots containing DNA from segregating individuals. The map position was determined using MAPMAKER/EXP 3.0 (Lander et al (1987) *Genomics* 1:174–181) by scoring 86 segregating progeny as homozygous parent A, as homozygous parent B, or as heterozygous. The map position was assigned to an existing core RFLP map of either of the following three populations: ALEB9 (240 individuals) DRAG2 (283 individuals) or MARS (1075 individuals). Table 3 shows the association of maize Mlo homologues and disease related loci and QTLS.

TABLE 1

BestFit (Similarity/Identity)

| Maize MLO Gene | HvMLO1 | ZmMLO1 | ZmMLO2 | ZmMLO4 | ZmMLO5 | ZmMLO6 | ZmMLO7 | ZmMLO8 | ZmMLO9 |
|---|---|---|---|---|---|---|---|---|---|
| | | | | Protein (Similarity/Identity) to: | | | | | |
| HvMLO1 | 100% | 67 | 53 | 35 | 45 | 58 | 40 | 44 | 37 |
| ZmMLO1 | 72 | 100% | 45 | 35 | 38 | 51 | 39 | 43 | 39 |
| ZmMLO2 | 61 | 56 | 100% | 40 | 48 | 58 | 43 | 46 | 40 |
| ZmMLO4 | 47 | 44 | 49 | 100% | 46 | 38 | 39 | 40 | 46 |
| ZmMLO5 | 54 | 47 | 56 | 56 | 100% | 45 | 50 | 76 | 41 |
| ZmMLO6 | 66 | 61 | 66 | 48 | 51 | 100% | 41 | 43 | 39 |
| ZmMLO7 | 48 | 49 | 52 | 48 | 58 | 52 | 100% | 56 | 41 |
| ZmMLO8 | 54 | 55 | 56 | 52 | 81 | 54 | 64 | 100% | 43 |
| ZmMLO9 | 48 | 48 | 49 | 51 | 56 | 50 | 51 | 56 | 100% |

TABLE 2

Gap (Similarity/Identity)

| Maize MLO Gene | HvMLO1 | ZmMLO1 | ZmMLO2 | ZmMLO4 | ZmMLO5 | ZmMLO6 | ZmMLO7 | ZmMLO8 | ZmMLO9 |
|---|---|---|---|---|---|---|---|---|---|
| | | | | Protein Homology (Similarity/Identity) to: | | | | | |
| HvMLO1 | 100% | 66 | 43 | 31 | 33 | 55 | 36 | 40 | 32 |
| ZmMLO1 | 71 | 100% | 36 | 24 | 32 | 43 | 28 | 37 | 28 |
| ZmMLO2 | 53 | 46 | 100% | 36 | 36 | 57 | 39 | 45 | 34 |
| ZmMLO4 | 42 | 31 | 46 | 100% | 32 | 34 | 35 | 37 | 42 |
| ZmMLO5 | 40 | 38 | 42 | 38 | 100% | 43 | 42 | 60 | 36 |
| ZmMLO6 | 63 | 51 | 64 | 43 | 49 | 100% | 40 | 41 | 36 |
| ZmMLO7 | 43 | 35 | 47 | 43 | 48 | 51 | 100% | 51 | 40 |
| ZmMLO8 | 49 | 48 | 54 | 49 | 67 | 52 | 59 | 100% | 40 |
| ZmMLO9 | 40 | 36 | 42 | 53 | 48 | 46 | 44 | 51 | 100% |

TABLE 3

Association of Maize MLO Homologues and Disease Related Loci and QTLs

| Maize MLO Homologue | | Nearby Disease Resistance Loci or QTLs |
|---|---|---|
| ZmMLO1 1.01 | 1.01 | European Corn Borer QTL |
| | 1.01/2 | Nortbern Corn Leaf Blight QTL |
| ZmMLO2 1.04 | 1.03/6 | Northern Corn Leaf Blight QTL |
| | 1.04 | Gray Leaf Spot QTL |
| | 1.04 | Maize Streak Virus (msvI) |
| | 1.05 | Stewart's Wilt QTL |
| ZmMLO4 3.05 | 3.04/5 | European Corn Borer QTL |
| | 3.04/5 | Gibberella Stalk Rot QTL |
| ZmMLO5 3.06 | 3.07/8 | Northern Corn Leaf Blight QTL |
| ZmMLO6a 5.05 | 5.04 | Gibberella Stalk Rot QTL |
| | 5.06 | Northern Corn Leaf Blight QTL |
| ZmMLO6b 6.02/3 | 6.01 | Southern Corn Leaf Blight (rhm1) |
| ZmMLO7 6.05/7 | | |
| ZmMLO8 9.04 | 9.05 | Southwestern Corn Borer QTL |
| ZmMLO9 na | | |

TABLE 4

Mutator Insertion Mutants of ZmMLO Homologues (TUSC)

ZmMLO2

| | |
|---|---|
| PV03 81D3 | *C. heterostrophus* intermediate resistance (segregating as recessive) |
| PV03 81D2 (sib) | *C. heterostrophus* intermediate resistance (segregating as recessive) |
| PV03 108B1 | *C. heterostrophus* intermediate resistance (segregating as recessive) |
| PV03 108A1 (sib) | *C. heterostrophus* resistance (segregating as recessive) |
| BT94 5F11 | *C. heterostrophus* resistance (segregating as recessive); also leaf necrosis |

The Trait Utility System for corn (TUSC) system was utilized to generate transposon mutants in the Mlo sequences in maize. The combination of transposon mutagenesis via Mutator and PCR-based selection of target-specific Mu insertions makes up the TUSC system. See, for example, Benson et al. (1995) *Plant Cell.* 7:75–84; Mena et al. (1996) *Science* 274:1537–1540; U.S. patent application Ser. No. 08/835,638 and U.S. patent application Ser. No. 08/262,056; all of which are herein incorporated by reference. Table 4 shows Mutator insertion mutants of ZmMlo homologues.

Oligonucleotide primers based on Mlo maize sequences were designed and paired with Mu TIR primer in PCR reactions. The products of the screening process identify individuals in the collection having Mu elements inserted into Mlo sequences.

The gene-specific primers used for TUSC of ZmMLO2 are: 19005, 5'-AGTTATCCAAGGCATGCCGGTGGTAAAACT-3' (SEQ ID NO18); and 19007, 5'-AAGTCATCGAGGGAGGCATCACTTACAG-3' (SEQ ID NO:19). For TUSC the mutator-element specific primer used was: 9242, 5'-AGAGAAGCCAACGCCA(AT)CGCCTC(CT)ATTTCGTC-3' (SEQ ID NO:20). Seven positive "hits" to ZmMLO2 were identified. Twenty F2 seeds for each of the hits were planted in the greenhouse and screened as follows. Seeds were planted in trays, containing 2-inch wells for each seed, in Strong-Lite (circleR) Universal Mix potting soil (Universal Mix, Pine Bluff, Ark., U.S.A.) and grown in a greenhouse (16 hour day, 20.6–34.8° C., 50% average RH, 560–620 microEinsteins, of light both sun and halogen lamps, averaging 25 heat units per day. Plants were grown for 14–18 days until the V5 stage (ca. 25 cm height) and inoculated with spores of *Cochliobolus heterostrophus* (Drechs.) Dreshs. Race 0, also known as *Bipolaris maydis* (Southern Leaf Blight) and *Cochliobolus carbonum* R. R Nelson, also known as *Bipolaris zeicola* (Helminthosporium Leaf Spot). For general leaf inoculation, spore suspensions of $4\times10^4$ per ml of 0.02% Tween-20 were sprayed as an aerosol on the leaves. Approximately 0.5 ml were applied per leaf late in the afternoon. The plants were then immediately covered with a plastic tent and kept at R.T. in order to enhance humidity and spore germination. The plastic tent was removed early in the morning, and the plants were returned to the greenhouse for the duration of the experiment, usually three days. Susceptibility to *Cochliobolus carbonum* was determined by either increased size or number of lesions. Resistance to *Cochliobolus heterostrophus* was determined by either reduced size or number of lesions. Lesion mimics were also investigated; these mutations form spontaneous lesions in the absence of pathogen attach. Other phenotypes affecting growth and development were also noted.

TABLE 5

| Gene Mapping | Maize MLO Gene | | | | | | | | |
|---|---|---|---|---|---|---|---|---|---|
| Information | ZmMLO1 | ZmMLO2 | ZmMLO4 | ZmMLO5 | ZmMLO6a | ZmMLO6b | ZmMLO7 | ZmMLO8 | ZmMLO9 |
| Gene Complexity on Southern blot | 1 | 1 | 1 | 1 | 2 | 2 | 1 | 1, 2 | 1, 2 |
| Chromosome location (bin) | 1.01 | 1.04 | 3.05 | 3.06 | 5.05 | 6.02/3 | 9.04 | 6.05/7 | unassigned |
| Chromosorne location (arm) | 1S | 1S | 3L | 3L | 5L | 6L | 9L | 6L | |
| Nearby Public Marker | BnI5.62 | BnI12.06 | ume10 | bnI10.24 | umc43 | ume113 | umc95 | bnI5.47 | |
| Distance from Public Marker | 12.3 (down) | 10.1 (down) | 6.5 (down) | 1.3 (up) | 10.9 (down) | 52.0 (up) | 6.3 (down) | 10.1 (up) | |
| Distance | 15 | 5.9 | 35.2 | 1.3 | 1.8 | 52 | 10.7 | 10.1 | |
| LOD Score | 18.2 | 24.1 | 21.3 | 31.7 | 35.2 | 4.6 | 36.5 | 23.8 | |
| RFLP Restriction Enzyme | EcoRI | HindIII | EcoRV | EcoRI | BamHI | BamHI | HindIII | EcoRV | |
| Mapping Population | ALEB9 | ALEB9 | DRAG2 | ALEB9 | DRAG2 | DRAG2 | DRAG2 | DRAG2 | DRAG2 |
| Mapping Parents (Public Names) | R67/P38 | R67/P38 | 17J/MWO | R67/P38 | 17J/MWO | 17J/MWO | 17J/MWO | 17J/MWO | 17J/MWO |

TABLE 6

| | Maize MLO Gene | | | | | | | | |
|---|---|---|---|---|---|---|---|---|---|
| Protein Structure Predictions | HvMLO1 | ZmMLO1 | ZmMLO2 | ZmMLO4 | ZmMLO5 | ZmMLO6 | ZmMLO7 | ZmMLO8 | ZmMLO9 |
| Protein Structure Predictions | | | | | | | | | |
| Number of amino acids | 533 | 224+ | 565 | 509 | 149+ | 515 | 499 | 492 | 469+ |
| Calculated molecular weight | 60,408 | | 64,274 | 58,613 | | 56,980 | 56,806 | 55,500 | |
| Calculated pl | 9.7 | | 9.6 | 9.3 | | 9.5 | 8.9 | 9.3 | |
| Number of transmembrane domains | 6 or 7 | | 6 or 7 | 6 or 7 | | 6 or 7 | 6 or 7 | 6 or 7 | |

TABLE 6-continued

| | Maize MLO Gene | | | | | | | | |
|---|---|---|---|---|---|---|---|---|---|
| Protein Structure Predictions | HvMLO1 | ZmMLO1 | ZmMLO2 | ZmMLO4 | ZmMLO5 | ZmMLO6 | ZmMLO7 | ZmMLO8 | ZmMLO9 |
| Glycosylation sites? Asn-X-Ser/Thr | 0 | 0 | i | 3 | 2 | 1 | 1 | 0 | |
| Signal Peptide | No | No | No | No | No | No | No | No | No |

EXAMPLE 1

Transformation and Regeneration of Transgenic Plants

Figure 3:
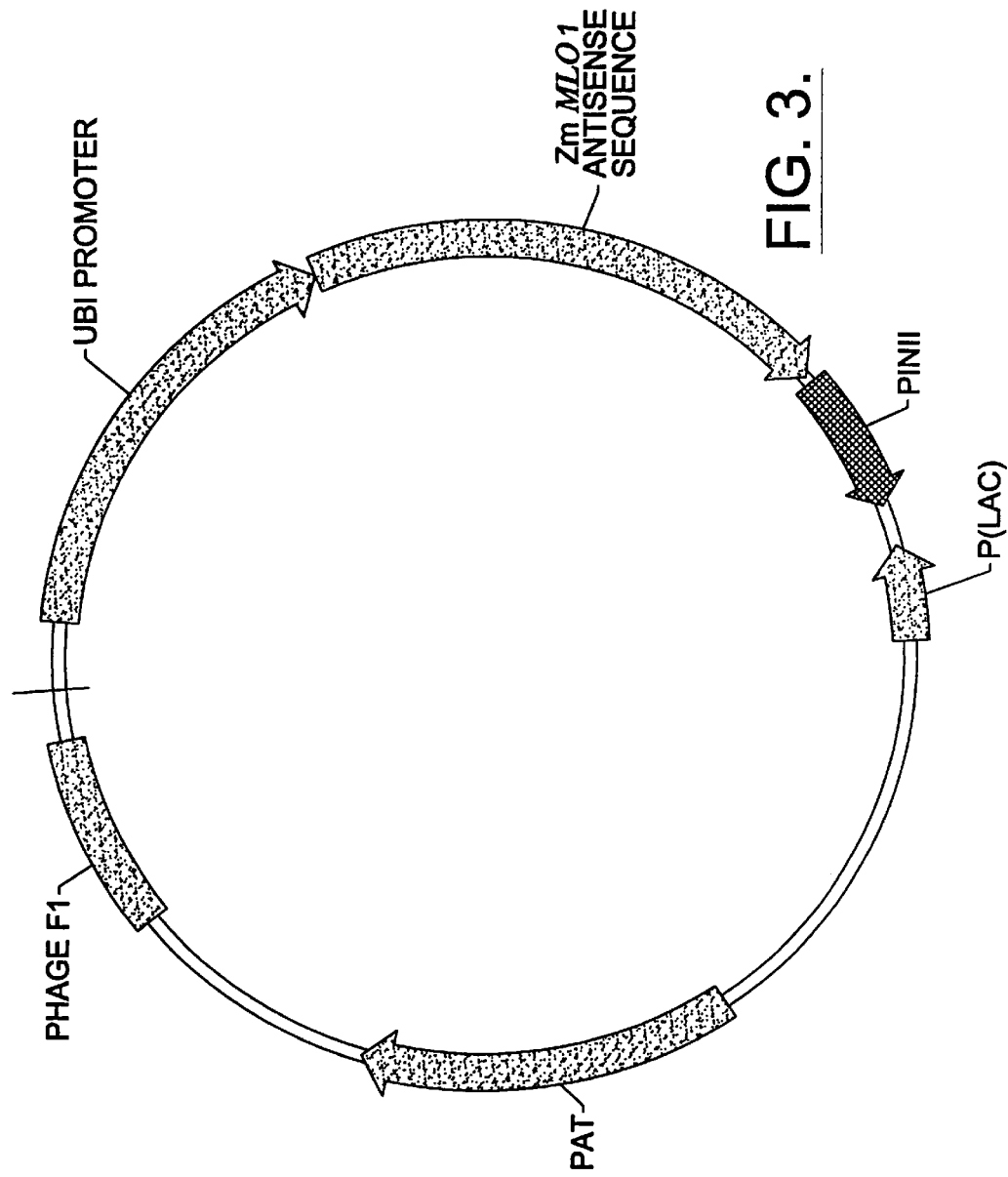
FIG. 3 schematically illustrates a plasmid vector comprising the ZmMlo 1 antisense construct operably linked to the ubiquition promoter.

Immature maize embryos from greenhouse donor plants are bombarded with a plasmid containing the ZmMLO1 antisense sequence operably linked to the ubiquitin promoter (FIG. 3). This plasmid also contains the selectable marker gene PAT (Wohlleben et al. (1988) *Gene* 70:25–37) that confers resistance to the herbicide Bialophos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the PAT selectable marker and the ZmMlo1 antisense sequence operably linked to a the ubiquitin is made and precipitated onto 1.1 $\mu$m (average diameter) tungsten pellets using a $CaCl_2$ precipitation procedure as follows:

100 $\mu$l prepared tungsten particles in water
10 $\mu$l (1 $\mu$g) DNA in TrisEDTA buffer (1 $\mu$g total)
100 $\mu$l 2.5 M $CaCl_2$
10 $\mu$l 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34- 1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance as a result of antisense disruption of ZmMlo1function.

272 V

| Ingredient | Amount | Unit |
|---|---|---|
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:

@=Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L)=1.00

288 J

| Ingredient | Amount | Unit |
|---|---|---|
| D-I $H_2O$ | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:

@=Add after bringing up to volume

Dissolve ingredients in polished D-I $H_2O$ in sequence

Adjust to pH 5.6

Bring up to volume with polished D-I H$_2$O after adjusting pH

Sterilize and cool to 60° C.

Add 3.5g/L of Gelrite for cell biology.

=Dissolve 0.100 g of Nicotinic Acid; 0.020 g of Thiamine.HCL; 0.100 g of

Pyridoxine.HCL; and 0.400 g of Glycine in 875.00 ml of polished D-I H$_2$O in sequence.

Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.

Total Volume (L)=1.00

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA- 1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:

@=Add after bringing up to volume

=Add after sterilizing and cooling to temp.

Dissolve ingredients in D-I H$_2$O in sequence

Adjust to pH 5.8 with KOH

Bring up to volume with D-I H$_2$O

Sterilize and cool to room temp.
Total Volume (L)=1.00

560 Y

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:

@=Add after bringing up to volume

=Add after sterilizing and cooling to temp.

Dissolve ingredients in D-I H$_2$O in sequence

Adjust to pH 5.8 with KOH

Bring up to volume with D-I H$_2$O

Sterilize and cool to room temp.

Autoclave less time because of increased sucrose

Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for creating or enhancing disease resistance in a plant, said method comprising modulating the expression of an *Mlo* nucleotide sequence wherein said nucleotide sequence is selected from the group consisting of:

(a) a nucleotide sequence encoding at least one of the maize MLO amino acid sequences selected from the group consisting of the sequences set forth in SEQ ID NOS: 4, 8, 12, and 16;

(b) a nucleotide sequence comprising at least one nucleotide sequence selected from the group consisting of the nucleotide sequences set forth in SEQ ID NOS: 3, 7, 11, and 15;

(c) a nucleotide sequence deposited in the American Type Culture Collection as Accession No. 98725 or 98728;

(d) a nucleotide sequence comprising an antisense sequence corresponding to a sequence of a), b), or c);

(e) a nucleotide sequence encoding an MLO protein and which hybridizes under high stringency conditions to at least one nucleotide sequence selected from the group consisting of the nucleotide sequences set forth in a), b), c), and d); and (f) a nucleotide sequence encoding an MLO protein and comprising at least 80% sequence identity to the nucleotide sequence of a).

2. The method of claim 1, wherein said modulation comprises decreasing the expression of the Mlo sequence.

3. The method of claim 1, wherein said plant is a monocot.

4. The method of claim 3, wherein said monocot is maize.

5. A modified plant having altered levels of an MLO protein wherein said plant has stably incorporated into its genome a DNA construct, wherein said DNA construct comprises a nucleotide sequence operably linked to a promoter capable of regulating transcription of said sequence in said plant, wherein said nucleotide sequence is selected from the group consisting of:

(a) a nucleotide sequence encoding at least one of the maize MLO amino acid sequences selected from the group consisting of the sequences set forth in SEQ ID NOS: 4, 8, 12, and 16;

(b) a nucleotide sequence comprising at least one nucleotide sequence selected from the group consisting of the nucleotide sequences set forth in SEQ ID NOS: 3, 7, 11, and 15;

(c) a nucleotide sequence deposited in the American Type Culture Collection as Accession No. 98725 or 98728;

(d) a nucleotide sequence comprising an antisense sequence corresponding to a sequence of a), b) or c);

(e) a nucleotide sequence encoding an MLO protein and comprising at least 80% sequence identity to at least one nucleotide sequence selected from the group consisting of the nucleotide sequences set forth in a), b), c) and d); and (f) a nucleotide sequence encoding an MLO protein and which hybridizes under high stringency conditions to at least one nucleotide sequence selected from the group consisting of the nucleotide sequences set forth in a), b), c), and d).

6. The modified plant of claim 5, wherein said plant exhibits a decrease in the expression of a Mlo gene.

7. The modified plant of claim 5, wherein said plant is a monocot.

8. The modified plant of claim 7, wherein said monocot is maize.

9. The maize plant of claim 8, wherein said plant has decreased levels of the Mlo protein.

10. The maize plant of claim 8, wherein said maize plant comprises an insertion sequence in at least one maize Mlo gene.

11. Seed of the plant of any one of claims 5, 6, 7, 8, 9, and 10, wherein said seed comprises said DNA construct.

12. An isolated nucleotide sequence said sequence selected from the group consisting of:

(a) a nucleotide sequence encoding at least one of the maize MLO amino acid sequences selected from the group consisting of the sequences set forth in SEQ ID NOS: 4, 8, 12, and 16;

(b) a nucleotide sequence comprising at least one nucleotide sequence selected from the group consisting of the nucleotide sequences set forth in SEQ ID NOS: 3, 7, 11, and 15;

(c) a nucleotide sequence deposited in the American Type Culture Collection as Accession No. 98725 or 98728;

(d) a nucleotide sequence comprising an antisense sequence corresponding to a sequence of a), b) or c);

(e) a nucleotide sequence encoding an MLO protein and comprising at least 80% sequence identity to at least one nucleotide sequence selected from the group consisting of the nucleotide sequences set forth in a), b), c) and d); and (f) a nucleotide sequence encoding an MLO protein and which hybridizes under high stringency conditions to at least one nucleotide sequence selected from the group consisting of the nucleotide sequences set forth in a), b), c), and d).

13. A modified plant cell having an altered level of an MLO protein wherein said plant cell has stably incorporated into its genome a DNA construct, wherein said DNA construct comprises a nucleotide sequence operably linked to a promoter capable of regulating transcription of said sequence in said plant cell, wherein said nucleotide sequence is selected from the group consisting of:

(a) a nucleotide sequence encoding at least one of the maize MLO amino acid sequences selected from the group consisting of the sequences set forth in SEQ ID NOS: 4, 8, 12, and 16;

(b) a nucleotide sequence comprising at least one nucleotide sequence selected from the group consisting of the nucleotide sequences set forth in SEQ ID NOS: 3, 7, 11, and 15;

(c) a nucleotide sequence deposited in the American Type Culture Collection as Accession No. 98725 or 98728;

(d) a nucleotide sequence comprising an antisense sequence corresponding to a sequence of a), b) or c);

(e) a nucleotide sequence encoding an MLO protein and comprising at least 80% sequence identity to at least one nucleotide sequence selected from the group consisting of the nucleotide sequences set forth in a), b), c) or d); and (f) a nucleotide sequence encoding an MLO protein and which hybridizes under high stringency conditions to at least one nucleotide sequence selected from the group consisting of the nucleotide sequences set forth in a), b), c), and d).

14. The modified plant cell of claim 13, wherein said cell exhibits a decrease in the expression of an Mlo gene.

15. The modified plant cell of claim 13, wherein said cell is from a monocot.

16. The modified plant cell of claim 15, wherein said monocot is maize.

17. A method for creating or enhancing disease resistance in a plant, said method comprising modulating the expression of an *Mlo* nucleotide sequence, wherein said nucleotide sequence is selected from the group consisting of:

(a) a nucleotide sequence encoding at least one of the maize *Mlo* amino acid sequences selected from the group consisting of the sequences set forth in SEQ ID NOS: 4, 8, 12, and 16; and (b) a nucleotide sequence comprising at least one nucleotide sequence selected from the group consisting of the nucleotide sequences set forth in SEQ ID NOS: 3, 7, and 15.

18. A method for creating or enhancing disease resistance in a plant, said method comprising modulating the expression of an *Mlo* nucleotide sequence, wherein, said nucleotide sequence encodes an MLO protein and comprises at least 85% sequence identity to at least one nucleotide sequence selected from the group consisting of the nucleotide sequences set forth in SEQ ID NOS: 3, 7, 11, and 15.

19. The method of claim 18, wherein said sequence identity is at least 90%.

20. The method of claim 18, wherein said sequence identity is at least 95%.

21. The method of claim 18, wherein said sequence identity is at least 98%.

22. A modified plant having altered levels of an MLO protein wherein said plant has stably incorporated into its genome a DNA construct, wherein said DNA construct comprises a nucleotide sequence operably linked to a promoter capable of regulating transcription of said sequence in said plant, wherein said nucleotide sequence is selected from the group consisting of:

(a) a nucleotide sequence encoding at least one of the maize MLO amino acid sequences selected from the group consisting of the sequences set forth in SEQ ID NOS: 4, 8, 12, and 16; and (b) nucleotide sequence comprising at least one nucleotide sequence selected from the group consisting of the nucleotide sequences set forth in SEQ ID NOS: 3, 7, 11, and 15.

23. Seed of the plant of claim 22, wherein said seed comprises said DNA construct.

24. A modified plant having altered levels of an MLO protein wherein said plant has stably incorporated into its genome a DNA construct, wherein said DNA construct comprises a nucleotide sequence operably linked to a promoter capable of regulating transcription of said sequence in said plant, wherein said nucleotide sequence encodes an MLO protein and comprises at least 85% sequence identity to at least one nucleotide sequence selected from the group consisting of the nucleotide sequences set forth in SEQ ID NOS: 3, 7, 11, and 15.

25. The modified plant of claim 24, wherein said sequence identity is at least 90%.

26. Seed of the plant of claim 25, wherein said seed comprises said DNA construct.

27. The modified plant of claim 24, wherein said sequence identity is at least 95%.

28. Seed of the plant of claim 27, wherein said seed comprises said DNA construct.

29. The modified plant of claim 24, wherein said sequence identity is at least 98%.

30. Seed of the plant of claim 29, wherein said seed comprises said DNA construct.

31. Seed of the plant of claim 24, wherein said seed comprises said DNA construct.

32. An isolated nucleotide sequence said sequence selected from the group consisting of:

(a) a nucleotide sequence encoding at least one of the maize MLO amino acid sequences selected from the group consisting of the sequence, set forth in SEQ ID NOS: 4, 8, 12, and 16; and (b) a nucleotide sequence comprising at least one nucleotide sequence selected from the group consisting of the nucleotide sequences set forth in SEQ ID NOS. 3, 7, 11, and 15.

33. An isolated nucleotide sequence encoding an MLO protein and comprising at least 85% sequence identity to at least one nucleotide sequence selected from the group consisting of the nucleotide sequences set forth in SEQ ID NOS: 3, 7, 11, and 15.

34. The isolated nucleotide sequence of claim 33, wherein said sequence identity is at least 90%.

35. The isolated nucleotide sequence of claim 33, wherein said sequence identity is at least 95%.

36. The isolated nucleotide sequence of claim 33, wherein said sequence identity is at least 98%.

37. A modified plant cell having an altered level of an MLO protein wherein said plant cell has stably incorporated into its genome a DNA construct, wherein said DNA construct comprises a nucleotide sequence operably linked to a promoter capable of regulating transcription of said sequence in said plant cell, wherein said nucleotide sequence is selected from the group consisting of:

(a) a nucleotide sequence encoding at least one of the maize MLO amino acid sequences selected from the group consisting of the sequences set forth in SEQ ID NOS: 4, 8, 12, and 16; and (b) a nucleotide sequence comprising at least one nucleotide sequence selected from the group consisting of the nucleotide sequences set forth in SEQ ID NOS: 3, 7, 11, and 15.

38. A modified plant cell having an altered level of an MLO protein wherein said plant cell has stably incorporated into its genome a DNA construct, wherein said DNA construct comprises a nucleotide sequence operably linked to a promoter capable of regulating transcription of said sequence in said plant cell, wherein said nucleotide sequence encodes an MLO protein and comprises at least 85% sequence identity to at least one nucleotide sequence selected from the group consisting of the nucleotide sequences set forth in SEQ ID NOS, 3, 7, 11, and 15.

39. The modified plant cell of claim 38, wherein said sequence identity is at least 90%.

40. The modified plant cell of claim 38, wherein said sequence identity is at least 95%.

41. The modified plant cell of claim 38, wherein said sequence identity is at least 98%.

* * * * *

UNITED STATES PATENT AND TRADEMARK OFFICE
CERTIFICATE OF CORRECTION

PATENT NO.     : 6,576,814 B1
DATED          : June 10, 2003
INVENTOR(S)    : Briggs et al.

It is certified that error appears in the above-identified patent and that said Letters Patent is hereby corrected as shown below:

Column 65,
Line 22, "MIo" should read -- MLO --;
Line 28, "7, and 15." should read -- 7, 11, and 15. --;
Line 53, after "(b)" insert -- a --.

Column 66,
Line 19, "sequence," should read -- sequences --.

Signed and Sealed this

Fourteenth Day of October, 2003

JAMES E. ROGAN
*Director of the United States Patent and Trademark Office*